(12) United States Patent
Berd

(10) Patent No.: US 6,458,369 B1
(45) Date of Patent: Oct. 1, 2002

(54) COMPOSITION COMPRISING TUMOR CELLS AND EXTRACTS AND METHOD OF USING THEREOF

(75) Inventor: David Berd, Wyncote, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/304,859

(22) Filed: May 4, 1999

Related U.S. Application Data

(60) Provisional application No. 60/084,081, filed on May 4, 1998.

(51) Int. Cl.$^7$ .................. A61K 45/00; A61K 39/00; A61K 39/38; A61K 39/388

(52) U.S. Cl. .................. 424/277.1; 424/184.1; 424/193.1; 424/278.1; 424/520; 424/573; 435/325

(58) Field of Search ............. 424/184.1, 193.1, 424/277.1, 278.1, 520, 573; 435/325

(56) References Cited

U.S. PATENT DOCUMENTS 5,290,551 A * 3/1994 Berd ................ 424/88
5,478,556 A * 12/1995 Elliot et al. ........ 424/852

FOREIGN PATENT DOCUMENTS

WO    WO 96/40173    12/1996 .......... A61K/35/12

OTHER PUBLICATIONS

Berd et al., Cancer Resaerch, vol. 51, pp. 2731–2734, May 15, 1991.*

Humphrey et al., Surgery, Gynecology, and Obstetrics, vol. 132, pp. 437–442, 1971.*

Mankiewicz et al., Cancer Immunology and Immunotherapy, vol. 2, pp. 27–39, 1977.*

Berd, D., Proceedings of the American Association for Cancer Research Annual Meeting, vol. 39, pp. 356, 1998.

Berd, D., Journal of Clinical Oncology, vol. 14, No. 6, pp. 2359–2370, 1997.

Berd, D., Proceedings of the American Association for Cancer Research Annual Meeting, vol. 35, pp. 667–668, 1994.

Berd, D., Proceedings of the American Association for Cancer Research Annual Meeting, vol. 36, pp. 677, 1995.

Berd et al., Proceedings of ASCO, vol. 16, p. 438a, 1997.

* cited by examiner

*Primary Examiner*—Sheela Huff
*Assistant Examiner*—Jennifer Hunt
(74) *Attorney, Agent, or Firm*—Darby & Darby

(57) ABSTRACT

The present invention is directed to compositions containing hapten-modified tumor cells and extracts and methods of treating cancer by administering a therapeutically effective amount of a composition containing a tumor cell or tumor cell extract to a subject in need of such treatment. The tumor cells and extracts of the invention and compositions thereof are capable of eliciting T lymphocytes that have a property of infiltrating a mammalian tumor, eliciting an inflammatory immune response to a mammalian tumor, eliciting a delayed-type hypersensitivity response to a mammalian tumor and/or stimulating T lymphocytes in vitro. The invention also relates to an effective vaccination schedule useful for inducing an antitumor response in a mammalian patient suffering from cancer by inducing at least one of the following: tumor necrosis, tumor regression, tumor inflammation, tumor infiltration by activated T lymphocytes, delayed-type hypersensitivity response, and prolongation of patient survival.

14 Claims, 19 Drawing Sheets

COMPOSITION COMPRISING TUMOR CELLS AND EXTRACTS AND METHOD OF USING THEREOF

This application claims priority under 35 U.S.C. §119 based upon provisional patent application No. 60/084,081 filed May 4, 1998, the entire disclosure of which is hereby incorporated by reference.

FIELD OF THE INVENTION

The present invention is directed to compositions comprising hapten-modified tumor cells and extracts and methods of treating cancer by administering a therapeutically effective amount of a composition comprising a tumor cell or tumor cell extract to a subject in need of such treatment. The invention also relates to an effective vaccination schedule useful for inducing an antitumor response in a patient suffering from cancer.

BACKGROUND OF THE INVENTION

It was theorized in the 1960's that tumor cells bear specific antigens (TSA) which are not present on normal cells and that the immune response to these antigens might enable an individual to reject a tumor. It was later suggested that the immune response to TSA could be increased by introducing new immunological determinants on cells. Mitchison, *Transplant. Proc.*, 1970, 2, 92. Such a "helper determinant", which can be a hapten, a protein, a viral coat antigen, a transplantation antigen, or a xenogenous cell antigen, could be introduced into a population of tumor cells. The cells would then be injected into an individual who would be expected to be tolerant to the growth of unmodified tumor cells. Clinically, the hope was that an immunologic reaction would occur against the helper determinants, as a consequence of which the reaction to the accompanying TSA is increased, and tumor cells which would otherwise be tolerated are destroyed. Mitchison, supra, also suggests several modes of action of the helper determinants including 1) that the unmodified cells are merely attenuated, in the sense that their growth rate is slowed down or their susceptibility to immunologic attack increased; 2) that helper determinants merely provide points of attack and so enable the modified cells to be killed by an immune response not directed against TSA; 3) that the helper determinants have an adjuvant action such as binding to an antibody or promoting localization of the cells in the right part of the body for immunization, in particular, in lymph nodes.

Fujiwara et al., *J. Immunol.*, 1984, 132, 1571 showed that certain haptenized tumor cells, i.e., tumor cells conjugated with the hapten trinitrophenyl (TNP), could induce systemic immunity against unmodified tumor cells in a murine system, provided that the mice were first sensitized to the hapten in the absence of hapten-specific suppressor T cells. Spleen cells from the treated mice completely and specifically prevented the growth of tumors in untreated recipient animals. Flood et al;, *J. Immunol.*, 1987, 138, 3573 showed that mice immunized with a TNP-conjugated, ultraviolet light-induced "regressor" tumor were able to reject a TNP-conjugated "progressor" tumor that was otherwise non-immunologic. Moreover, these mice were subsequently resistant to challenge with unconjugated "progressor" tumor. In another experimental system, Fujiwara et al.,*J. Immunol.*, 1984, 133, 510 demonstrated that mice sensitized to trinitrochlorobenzene (TNCB) after cyclophosphamide pretreatment could be cured of large (10 mm) tumors by in situ haptenization of tumor cells; subsequently, these animals were specifically resistant to challenge with unconjugated tumor cells.

The teachings of Fujiwara et al. differ from the present invention for several reasons including the following: A. The cells used in Fujiwara's composition are derived from induced transplantable murine tumors—not from spontaneous human tumors; B. Fujiwara's composition is used in immunoprophylaxis—the present invention uses immunotherapy; C. Fujiwara's composition is administered as a local therapy—the composition of the present invention is administered by systemic inoculation; and D. Fujiwara's composition did not result in tumor regression—the composition of the present invention results in regression and/or prolonged survival for at least a substantial portion of the patients treated.

The existence of T cells which cross-react with unmodified tissues has recently been demonstrated. Weltzien and coworkers have shown that class I MHC-restricted T c6ell clones generated from mice immunized with TNP-modified syngeneic lymphocytes respond to MHC-associated, TNP-modified "self" peptides. Ortmann, B.,: et al., *J. Immunol.*, 1992, 148, 1445. In addition, it has been established that immunization of mice with TNP-modified lymphocytes results in the development of splenic T cells that exhibit secondary proliferative and cytotoxic responses to TNP-modified cells in vitro. Shearer, G. M. Eur. *J. Immunol.*, 1974, 4, 527. The potential of lymphocytes elicited by immunization with DNP- or TNP-modified autologous cells to respond to unmodified autologous cells is of considerable interest because it may be relevant to two clinical problems: 1) drug-induced autoimmune disease, and 2) cancer immunotherapy. In regard to the former, it has been suggested that ingested drugs act as haptens, which combine with normal tissue protein forming immunogenic complexes that are recognized by T cells. Tsutsui, H., et al.,*J. Immunol.*, 1992, 149, 706. Subsequently, autoimmune disease, e.g., systemic lupus erythematosus, can develop and continue even after withdrawal of absence of the offending drug. This would imply the eventual generation of T lymphocytes that cross-react with unmodified tissues.

The common denominator of these experiments is sensitization with hapten in a milieu in which suppressor cells are not induced. Spleen cells from cyclophosphamide pretreated, TNCB-sensitized mice exhibited radioresistant "amplified helper function" i.e., they specifically augmented the in vitro generation of anti-TNP cytotoxicity. Moreover, once these amplified helpers had been activated by in vitro exposure to TNP-conjugated autologous lymphocytes, they were able to augment cytotoxicity to unrelated antigens as well, including tumor antigens (Fujiwara et al., 1984). Flood et. al., (1987), supra, showed that this amplified helper activity was mediated by T cells with the phenotype $Lyt^-1^+$, $Lyt^-2^-$, $L3T4^+$, $I^-J^+$ and suggests that these cells were contrasuppressor cells, a new class of immunoregulatory T cell.

Immunotherapy of patients with melanoma had shown that administration of cyclophosphamide, at high dose (1000 $mg/M^2$) or low dose (300 $mg/M^2$), three days before sensitization with the primary antigen keyhole limpet hemocyanin markedly augments the acquisition of delayed type hypersensitivity to that antigen (Berd et al., *Cancer Res.*, 1982, 42, 4862; *Cancer Res.*, 1984, 44, 1275). Low dose cyclophosphamide pretreatment allows patients with metastatic melanoma to develop delayed type hypersensitivity to autologous melanoma cells in response to injection with autologous melanoma vaccine (Berd et al., *Cancer Res.*, 1986, 46, 2572; *Cancer Invest.,* 1988, 6, 335). Cyclophosphamide administration results in reduction of peripheral blood lymphocyte non-specific T suppressor function (Berd et al., *Cancer Res.,* 1984, 44, 5439; *Cancer Res.,* 1987, 47, 3317), possibly by depleting CD4+, CD45R+ suppressor inducer T cells (Berd et al., *Cancer Res.,* 1988, 48, 1671). The anti-tumor effects of this immunotherapy regimen appear to be limited by the excessively long interval between the initiation of vaccine administration and the development of delayed type hypersensitivity to the tumor cells (Berd et al., *Proc. Amer. Assoc. Cancer Res.,* 1988, 29, 408 (#1626)). Therefore, there remains a need to increase the therapeutic efficiency of such a vaccine to make it more immunogenic.

Most tumor immunologists now agree that infiltration of T lymphocytes, white cells responsible for tumor immunity, into the tumor mass is a prerequisite for tumor destruction by the immune system. Consequently, a good deal of attention has been focused on what has become known as "TIL" therapy, as pioneered by Dr. Stephen Rosenberg at NCI. Dr. Rosenberg and others have extracted from human cancer metastases the few T lymphocytes that are naturally present and greatly expanded their numbers by culturing them in vitro with Interleukin 2 (IL2), a growth factor for T lymphocytes. Topalian et al., *J. Clin. Oncol.,* 1988, 6, 839. However this therapy has not been very effective because the injected T cells are limited in their ability to "home" to the tumor site.

The ability of high concentrations of IL2 to induce lymphocytes to become non-specifically cytotoxic killer cells has been exploited therapeutically in a number of studies (Lotze et al., *J. Biol. Response,* 1982, 3, 475; West et al., *New Engl. J. Med.,* 1987, 316, 898). However, this approach has limitations due to the severe toxicity of high dose intravenous IL2. Less attention has been given to the observation that much lower concentrations of IL2 can act as an immunological adjuvant by inducing the expansion of antigen-activated T cells (Talmadge et al., *Cancer Res.,* 1987, 47, 5725; Meuer et al., *Lancet,* 1989, 1, 15). Therefore, there remains a need to understand and attempt to exploit the use of IL2 as an immunological adjuvant.

Human melanomas are believed to express unique surface antigens recognizable by T lymphocytes. Old, L. J., *Cancer Res.,* 1981, 41, 361; Van der Bruggen, P., et al., *Science,* 1991, 254, 1643; Mukherji, B., et al., *J. Immunol.,* 1986, 136, 1888; and Anichini, A., et al., *J. Immunol.,* 1989, 142, 3692. However, immunotherapeutic: approaches prior to work done by the present inventor had been limited by the difficulty of inducing an effective T cell-mediated response to such antigens in vivo.

There are several models proposed to explain what appears to be tolerance to human tumor-associated antigens. They include:

1) Tumor antigen-specific suppressor cells that down-regulated incipient anti-tumor responses. Mukherji, et al., supra; Berendt, M. J. and R. J. North., *J. Exp. Med.,* 1980, 151, 69.

2) Failure of human tumor cells to elicit T helper cells or to provide costimulatory signals to those T cells. Fearon, E. R., et al., *Cell,* 1990, 60, 397; Townsend, S. E. and J. P. Allison, *Science,* 1993, 259, 368; and 3) Reduced surface expression of major histocompatibility products: on tumor cells which limits their recognition by T cells. Ruiter, D. J., *Seminars in Cancer Biology,* 1991, 2, 35. None of these hypotheses has yet been corroborated in a clinical system.

The goal of active immunotherapy for tumors is the development of a productive systemic T cell mediated tumor-specific immunity. Tumor specific immunity would act both at the primary tumor site as well as in clearing small metastatic foci at distant sites. The generation of T cell immunity has been shown to be a highly regulated response requiring cell-cell interaction and the production of a number of cytokines. Of late, studies in a number of human and urine systems have shown that T cell responses can be separated into two categories termed Type I and II (Mossman, et al., *J. Immunol.* 1986 136:2348). Type I responses are required for the development of delayed type hypersensitivity (DTH), are associated with macrophase activation and the production of interferon-gamma (IFN$_\gamma$), and have been shown to be associated with the resolution of human leprosy (Yamamura, M., et al., *Science* 1991 254:277–279) and murine leishmaniasis (Scott, P., et al., *Immunological Review* 1989 112:161–182). Type II responses are associated with the production of IL4 and IL10, primarily support antibody responses, and are associated with the progressive forms of leprosy (Yamamura, M., et al., supra) and leishmaniasis (Yamamura et al., supra; and Scott, P., et al., supra.). In addition to the development of DTH, Type I responses would be expected to enhance the generation of tumor specific CTL via upregulation of MHC and tumor associated antigens as well as enhanced antigen presentation secondary to localized IFN$\gamma$ production. More recently, Type I and II response have been shown to be cross regulating: IFN$\gamma$ inhibits Type II responses, while IL4 and IL10 inhibit Type I (Scott, *J. Immunol.* 1991 147:3149–3155; and Fiorentino et al., *J. Immunol.* 1991 146:3444–3451). In the leishmania system, modulation of cytokines at the lesion site allows for the conversion of a Type II to a Type I response, and, consequently, a change from progressive infection to eradication of the disease (Scott, 1991, supra).

Pisa et al., *Proc. Natl. Acad. Sci. USA* 1992 89:7708–7712 detected IL10 mRNA in ovarian carcinoma biopsies, but not in ovarian carcinoma cell lines; they concluded that the source of IL10 was tumor-infiltrating lymphocytes. Gastl et al, *Int. J. Cancer* 1991 55:96–101 found that 16/48 tumor cell lines released IL10 into the culture supernatant; only 3–8 melanoma cell lines were positive. Finally, Chen et al., *Int. J. Cancer,* 1994 56:755–760 recently reported that 6/9 cell lines derived from metastatic melanomas expressed IL10 mRNA. However, the present invention is the first report known to the inventors of mRNA for IL10 in metastatic melanoma biopsies.

It is not known whether these observations are applicable to the human tumor-host relationship, i.e., whether the pattern of cytokine production by T cells infiltrating tumors is an indicator of the effectiveness of the immune response. Patients with metastatic melanoma treated with an autologous, DNP-modified vaccine develop inflammatory responses at tumor sites, Berd et al., 1991, supra. Histologically, these inflamed lesions are characterized by T cell infiltration which is sometimes associated with tumor cell destruction. The present invention finds that tumors from DNP-vaccine-treated patients contain Type I T lymphocytes, which are not detectable in tumors excised prior to vaccine administration.

Conventional attempts to treat human cancer have been unsuccessful or only partially successful, and often have undesirable side effects. Attempts to treat cancer based on various immunological theories have also been unsuccessful. Although the Applicant has successfully treated melanoma in certain patients using hapten-conjugated melanoma cells, there remains a need in the cancer treatment art for additional and improved methods for inducing an anti-tumor response. Applicant has now discovered an effective vaccination protocol using hapten-modified tumor cells or extracts.

SUMMARY OF THE INVENTION

The present invention relates to compositions containing hapten-modified tumor cells and tumor cell extracts and methods for inducing an antitumor response in a patient suffering from cancer by administering the compositions of the invention.

According to one aspect, the present invention relates to an isolated mammalian, preferably human, tumor cell or tumor cell extract modified with a hapten.

In another aspect, the present invention is directed to a composition comprising a hapten modified mammalian tumor cell or extract.

In yet another aspect, the invention provides for a vaccine composition comprising a therapeutically effective amount of a mammalian, preferably human, tumor cell or extract modified with a hapten.

In yet another aspect, the present invention is directed to a method of treating cancer comprising administering to a mammal, preferably a human, a composition comprising a therapeutically effective amount of a hapten modified human tumor cell or extract wherein said mammal suffers from a malignant tumor of the same type as said tumor cell membrane.

In a further aspect, the invention is directed to a method of treating cancer according to a weekly vaccination schedule.

BRIEF DESCRIPTION OF THE FIGURES

FIG. 11 shows graphs of cytotoxicity of DNP-reactive T cells. Melanoma cells, either autologous (autol) or allogeneic class I-mismatched (allo), were used as targets in a 6-hour "Cr assay. Effector cells were expanded CD8+, DNP-reactive T cells.

FIG. 14A shows mRNA for cytokines determined by RT-PCR (lane 1=size marker; 2=beta-actin; 3=IFNγ, 4=IL4; 5=IL10); FIG. 14B is an H&E stained section of the subcutaneous lesion (400X).

FIG. 15A shows mRNA for cytokines determined by RT-PCR (lane 1=size marker; 2=beta-actin; 3=IFNγ; 4=IL4; 5=IL10); FIG. 15B is an H&E stained section of the lymph node metastasis (400×).

FIG. 17 shows IL10 mRNA expression by RT-PCR from representative tumor biopsy and derived cell line (lane 1=size marker; 2=IL10 cDNA; 3=tumor biopsy; 4=tumor line).

DETAILED DESCRIPTION OF THE INVENTION

Figure 1:
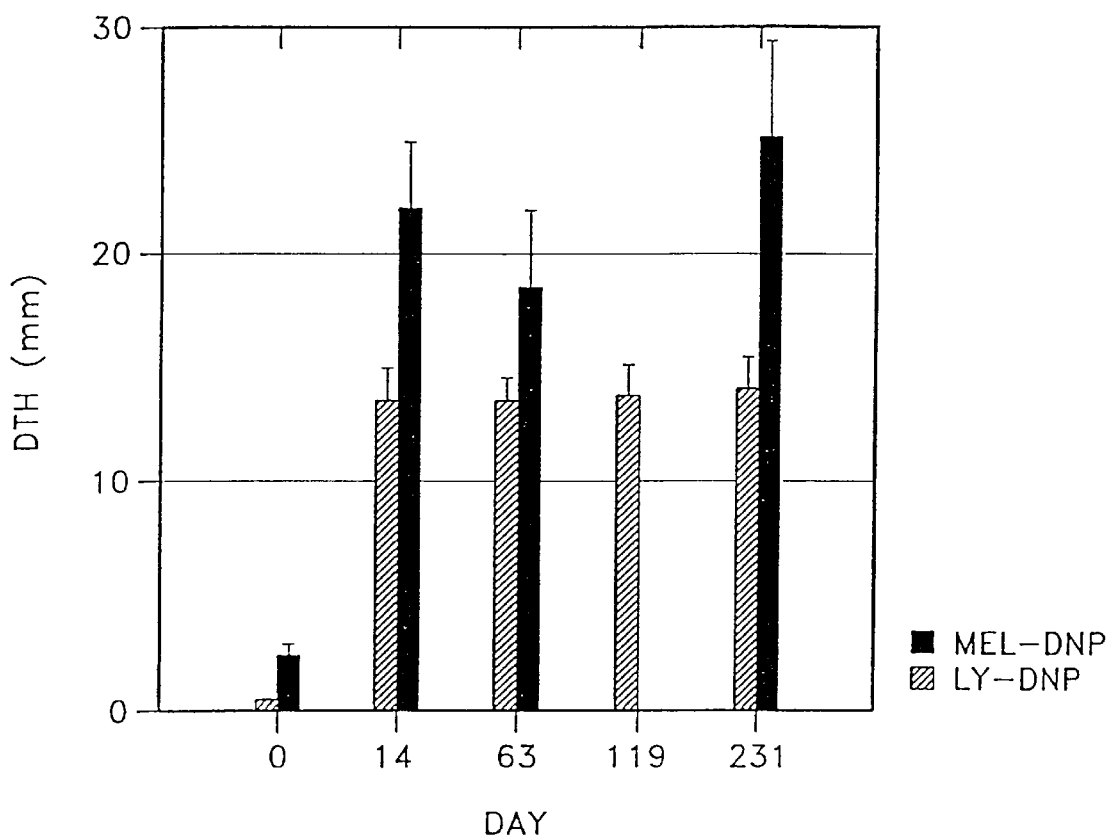
FIG. 1 displays the kinetics of the development of DTH to DNP-modified autologous PBL and melanoma cells. Patients with metastatic melanoma treated with DNP-vaccine were serially skin tested with DNP-modified PBL (LY) or DNP-modified melanoma cells dissociated from a metastatic mass (MEL). Each bar indicates the mean DTH response for the group of patients at each time point; error bars=standard error. For day 119, only responses to PBL were measured. Sample sizes: days 0, 14, 63, N=84; day 119, N=57; day 175, N=42; day 231, N=35.

The present invention is directed to cancer immunotherapy. A tumor composition and methods of treating cancer are included in the scope of the invention. The invention further relates to a method of inducing an antitumor response according to a weekly vaccination schedule. For purposes of the present invention an antitumor response is at least one of the following: tumor necrosis, tumor regression, tumor inflammation, tumor infiltration by activated T lymphocytes, delayed-type hypersensitivity response, and prolongation of patient survival. The tumor cells and extracts of the invention and compositions thereof are capable of eliciting T lymphocytes that have a property of infiltrating a mammalian tumor, eliciting an inflammatory immune response to a mammalian tumor, eliciting a delayed-type hypersensitivity response to a mammalian tumor and/or stimulating T lymphocytes in vitro.

An anti-tumor response resulting from the treatment according to the present invention may be a partial or a complete regression of the metastatic tumor or a stable disease. A "complete" regression indicates about 100% regression for a period of at least one month, more preferably for a period of at least three months. A "partial" regression indicates more than about 50% regression for a period of at least one month, more preferably for a period of at least three months. A "stable" disease indicates a condition in which there is no significant growth of the tumor after the vaccine treatment. Another anti-tumor response that may be observed upon following the treatment of the invention is prolongation of survival.

Any malignant tumor may be treated according to the present invention including metastatic and primary cancers and solid and non-solid tumors. Solid tumor include carcinomas, and non-solid tumors include hematologic malignancies. Carcinomas include and are not limited to adenocarcinomas and epithelial carcinomas. Hematologic malignancies include leukemias, lymphomas, and multiple myelomas. The following are non-limiting examples of the cancers treatable with isolated modified tumor cell membranes according to the methods of the present invention: ovarian, including advanced ovarian, leukemia, including and not limited to acute myelogenous leukemia, colon, including colon metastasized to liver, rectal, colorectal, melanoma, breast, lung, kidney, and prostate cancers. The ovarian cancers may be adenocarcinomas or epithelial carcinomas. Colon and prostate cancers are adenocarcinomas. Leukemias may originate from myeloid bone marrow or lymph nodes. Leukemias may be acute, exhibited by maturation arrest at a primitive stage of development, and chronic, exhibited by excess accrual of mature lymphoid or myeloid cells. Stage I, II, III, or IV cancer may be treated according to the present invention, preferably stages III and IV, even more preferably stage III. Any mammal, preferably a human, may be treated according to the present invention.

The compositions of the present invention are prepared from a tumor cell or tumor cell extract. A tumor cell may be a malignant or pre-malignant cell of any type of cancer. In accordance with the present invention, pre-malignant refers to any abnormal cell suggestive of a cancer cell, which is not yet a cancer cell; such as and not limited to dysplastic changes in cervical cells which ultimately lead to cervical cancer, and dysplastic nevi which are abnormal skin cells which lead to melanoma. The tumor cells and extracts preferably originate from the type of cancer which is to be treated. For example, a melanoma cell or cell extract is used to treat melanoma type cancer. The tumor cells and extracts may be, and are not limited to, autologous and allogenic cells dissociated from biopsy specimens or tissue culture, as well as stem cells and extracts from these sources. In one preferred embodiment, the cells and extracts are autologous. However, any non-allogeneic cell, including tumor cells produced in culture from autologous cells isolated from the patient's tumor, may be used. Tumor cells need not be completely (i.e., 100%) genetically identical to either the tumor cell or the non-tumor, somatic cell of the treated patient. Genetic identity of the MHC molecules between the tumor cell and the patient is generally sufficient. Additionally, there may be genetic identity between a particular antigen on the melanoma cell and an antigen present on the patient's tumor cells. Genetic identity may be determined according to the methods known in the art. For purposes of the present invention, a tumor cell that has been genetically altered (using for example recombinant DNA technology) to become genetically identical with respect to, for example, the particular MHC molecules of the patient and/or the particular antigen on the patient's cancer cells is within the meaning of "non-allogeneic" and within the scope of the present invention. Such cells may also be referred to as "MHC-identical" or "MHC-compatible."

Tumor cell extracts of the present invention may be a peptide isolated from a hapten modified cancer cell or a cell membrane isolated from a hapten modified cancer cell. Extracts may also be first isolated from tumor cells and then hapten modified.

For purposes of the present invention, peptides are compounds of two or more amino acids including proteins. Peptides will preferably be of low molecular weight, of about 1,000 kD to about 10,000 kD, more preferably about 1,000 to about 5,000, which are isolated from a haptenized tumor cell and which stimulate T cell lymphocytes to produce gamma interferon. T cells are lymphocytes which mediate two types of immunologic functions, effector and regulatory, secrete proteins (lymphokines), and kill other cells (cytotoxicity). Effector functions include reactivity such as delayed hypersensitivity, allograft rejection, tumor immunity, and graft-versus-host reactivity. Lymphokine production and cytotoxicity are demonstrated by T cell effector functions. Regulatory functions of T cells are represented by their ability to amplify cell-mediated cytotoxicity by other T cells and immunoglobulin production by B cells. The regulatory functions also require production of lymphokines. T cells produce gamma interferon (IFNγ) in response to an inducing stimulus including and not limited to mitogens, antigens, or lectins. The peptide may preferably be about 8 to about 20 amino acids, in addition the peptide is preferably haptenized. Peptides may be isolated front the cell surface, cell interior, or any combination of the two locations. The extract may be particular to type of cancer cell (versus normal cell). The peptide of the present invention includes and is not limited to a peptide which binds to the major histocompatibility complex, a cell surface-associated protein, a protein encoded by cancer oncogenes or mutated anti-oncogenes.

The cancer cell membrane of the present invention may be all or part of a membrane from a membrane isolated from a haptenized cancer cell. In accordance with the definition of cancer cell membrane as set forth for the present invention, a cancer cell membrane may be isolated then haptenized, alternatively, a cancer cell may be haptenized and the membrane subsequently isolated therefrom.

The cell extracts are able to stimulate T cells. Stimulation for purposes of the present invention refers to proliferation of T cells as well as production of cytokines by T cells, in response to the cell extract. Membranes and proteins isolated from hapten modified tumor cells and proteins each independently have the ability to stimulate T cells. Proliferation of T cells may be observed by uptake by T cells of modified nucleic acids, such as and not limited to 3H thymidine, $^{125}$IUDR (iododeoxyuridine); and dyes such as 3-(4,5-dimethylthiazol-2-yl)-2,5-diphenyltetrazolium bromide (MTT) which stains live cells. In addition, production of cytokines such as and not limited to IFN$\gamma$, tumor necrosis factor (TNF), and IL-2. Production of cytokines is preferably in an amount of greater than 15 picograms/ml, more preferably about 20 to about 30 picograms/ml, even more preferably about 50 picograms/ml.

Preferably, the tumor cell extract comprises cellular materials which are unique, or substantially specific to, a particular type of cancer. The tumor cells of the present invention may be live cells. In one preferred embodiment, the tumor cells and extracts of the present invention are incapable of growing in the body of the patient after injection. Method of preventing cells from growing are known to those of skill in the art. For example, tumor cells may be irradiated prior to use. In one embodiment, tumor cells or extracts are irradiated at about 2500 cGy to prevent the cells from growing after injection.

The compositions of the invention may be employed in the method of the invention singly or in combination with other compounds, including and not limited to other compositions of the invention. Accordingly, cancer cells and cancer cell extracts may be used alone or coadministered. For purposes of the present invention, co-administration includes administration together and consecutively. In addition, the cancer cell membrane may be co-administered with the peptide. Further, the cancer cells and/or extracts may be co-administered with other compounds including and not limited to cytokines such as interleukin2, interleukin-4, gamma interferon, interleukin-12, GM-CSF. The tumor cells and extracts of the invention may also be used in conjunction with other cancer treatments including and not limited to chemotherapy, radiation, antibodies, oligonucleotide sequences, and antisense oligonucleotide sequences.

The compositions of the invention may be administered in a mixture with a pharmaceutically-acceptable carrier, selected with regard to the intended route of administration and the standard pharmaceutical practice. Dosages may be set with regard to weight, and clinical condition of the patient. The proportional ratio of active ingredient to carrier naturally depend on the chemical nature, solubility, and stability of the compositions, as well as the dosage contemplated. Amounts of the tumor cells and extracts of the invention to be used depend on such factors as the affinity of the compound for cancerous cells, the amount of cancerous cells present and the solubility of the composition.

The composition of the present invention may be mixed with an immunological adjuvant and/or a pharmaceutically acceptable carrier. Any known aqueous vehicle useful in drug delivery, such as and not limited to saline, may be used in accordance with the present invention as a carrier. In addition, any adjuvant known to skilled artisans may be useful in the delivery of the present invention. The adjuvant has the property of augmenting an immune response to the tumor cell preparations of the present invention. Representative examples of adjuvants are BCG, or the synthetic adjuvant, QS-21 comprising a homogeneous saponin purified from the bark of *Quillaja saponaria, Corynebacterium parvum* (McCune et al., *Cancer* 1979 43:1619), saponins in general, detoxified endotoxin and cytokines such as interleukin-2, interleukin-4, gamma interferon (IFN-$\gamma$), interleukin-12, interleukin-15, GM-CSF and combinations thereof.

In the case where the cells and cell extracts are irradiated and haptenized, the cells may be conjugated to a hapten and then irradiated. Alternatively, the cells may be irradiated then conjugated to a hapten. In either case, the extracts are subsequently purified and then may also be irradiated and/or haptenized. To irradiate and haptenize the extracts, either method may be performed first, followed by the other method.

Alternatively, the tumor cells or tumor cell extracts may be added to antigen presenting cells. The cancer cell extract may be used to treat cancer together with another cell type, an antigen presenting cell, selected from the group consisting of autologous cultured macrophages and autologous cultured dendritic cells. Macrophages are any large ameboid mononuclear cell, regardless of origin, such as and not limited to histiocytes and monocytes, which phagocytose, i.e. engulf and destroy, other cells, dead tissue, degenerated cells, and the like. Macrophages are antigen presenting cells, which present antigens, including tumor antigens, to cells including T cells. Dendritic cells are also antigen presenting cells and appear to be closely related to macrophages, however, dendritic cells are more efficient antigen presenting cells than macrophages. They are potent stimulators of T cells and may be isolated from a variety of body organs and tissues including and not limited to blood, skin (where dendritic cells are referred to as Langerhans cells), lymphoid tissues.

The antigen presenting cells with peptide or membrane bound thereto, for example, may be used to immunize patients. The patient's blood is obtained and macrophages or dendritic cells are extracted therefrom. High concentrations of the peptide (about 1 ng/ml to about 1 $\mu$g/ml, preferably about 10 ng/ml to about 100 ng/ml), or membrane (about $10^5$ to about $10^7$ cell equivalents (c.e.), cell equivalents are in relation to the number of starting cells, i.e., the amount of cell extract obtained from the indicated number of cells) are incubated with the cells overnight or for about 8 hours. In the case of incubating with membranes, the membranes are phagocytized by the macrophages or dendritic cells. The macrophages or dendritic cells which have phagocytized the membranes are used to immunize the patient, Grabbe, S., et al., *Immunology Today* 1995 16:117–121, the disclosure of which is incorporated herein by reference in its entirety.

The vaccine composition of the invention may contain, for example, at least $10^4$ tumor cells or c.e. of tumor cell extract (e.g. isolated membrane or peptide) per dose, preferably at least $10^5$ cells/c.e. extract, and most preferably at least $10^6$ cells/c.e. extract. A dose is that amount of the vaccine composition that is administered in a single administration. In one embodiment, the vaccine composition contains from about $10^5$ to about $2.5 \times 10^7$ cells/c.e. extract per dose, more preferably about $5 \times 10^6$ cells/c.e. In one preferred embodiment, the vaccine composition contains a maximum of $7.5 \times 10^6$ cells/c.e. extract. The amount of the tumor cells and tumor cell membranes of the invention to be used generally depends on such factors as the affinity of the compound for cancerous cells, the amount of cancerous cells present and the solubility of the composition. Dosages may be set with regard to weight, and clinical condition of the patient.

The vaccine composition of the invention may be packaged in a dosage form suitable for intradermal, intravenous, intraperitoneal, intramuscular, and subcutaneous administration. Alternatively, the dosage form may contain the preparations of the invention (e.g. tumor cells, membranes, peptides) to be reconstituted at the time of the administration with, for example, a suitable diluent.

The tumor cells, tumor cell extracts and compositions thereof of the invention may be administered by any suitable route, including inoculation and injection, for example, intradermal, intravenous, intraperitoneal, intramuscular, and subcutaneous. There may be multiple sites of administration per each vaccine treatment. For example, the vaccine composition may be administered by intradermal injection into at least two, and preferably three, contiguous sites per administration. In one embodiment of the invention, the vaccine composition is administered on the upper arms or legs.

Prior to administration of the vaccine composition of the invention, the subject may be immunized to the hapten which is to be used to modify tumor cells and membranes by applying it to the skin. For example, dinitrofluorobenzene (DNFB) may be used. In one embodiment of the invention, the patient is not immunized to a hapten prior to vaccine administration. Subsequently (about two weeks later, for example), the subject may be injected with a tumor cell or extract composition. The composition may be administered (such as by reinjection) for a total of at least three and preferably at least six treatments. In one embodiment, the total number of administrations (including the initial administration) may be eight, and in another embodiment may be ten. The vaccination schedule may be designed by the attending physician to suit the particular subject's condition. The vaccine injections may be administered, for example, every 4 weeks, preferably every 2 weeks, and most preferably every week. In one preferred embodiment, the vaccine is injected every week for a total of six treatments. Haptenized and non-haptenized vaccine may be alternated. In one preferred embodiment, all vaccines contain hapten modified tumor cells or extracts. A booster vaccine may be administered. Preferably, one or two booster vaccines are administered. The booster vaccine may be administered, for example, after about six months or about one year after the initial administration.

The drug cyclophosphamide (CY) may be administered several days (e.g. 3 days) prior to each vaccine administration to augment the immune response to the tumor cells. In one preferred embodiment, CY is administered only prior to the first vaccine injection.

The vaccine of the present invention may be haptenized or non-haptenized. The haptenized, or chemically-linked, form of the vaccine may include a tumor cell haptenized to dinitrophenyl (DNP) for example. Other haptens include and are not limited to trinitrophenyl, N-iodoacetyl-N'-(5-sulfonic 1-naphthyl)ethylene diamine, trinitrobenzenesulfonic acid, fluorescein isothiocyanate, arsenic acid benzene isothiocyanate, trinitrobenzenesulfonic acid, sulfanilic acid, arsanilic acid, dinitrobenzene-S-mustard. Combinations of hapten may also be used. A vaccine of tumor cell extracts may similarly be haptenized. In the case of haptenized cancer cell extracts, the extracts, a peptide, and a cancer cell membrane, are isolated from haptenized cancer cells. The present invention also contemplates a non-haptenized vaccine of tumor cells and/or cell extracts.

In one embodiment of the present invention, a method of treating a patient suspected of having cancer, may comprise administering a pharmaceutically acceptable amount of cyclophosphamide, and a pharmaceutically acceptable amount of a composition selected from the group consisting of live tumor cells, tumor cell extracts, and a mixture of tumor cells and tumor cell extracts. Where the composition is a cancer cell extract, the extract may be a peptide or a membrane isolated from a haptenized cancer cell. The composition may be mixed with an immunological adjuvant and/or a pharmaceutically acceptable carrier. The haptenized vaccine may optionally be followed by administration of a pharmaceutically acceptable amount of a non-haptenized vaccine. A nonhaptenized vaccine may also be administered in accordance with the methods of the present invention.

In another embodiment of the invention, the composition of the invention is administered every week for a period of at least six weeks, and the first administration is preceded by a pharmaceutically acceptable amount of cyclophosphamide. Preferably, the composition may contain a maximum of about $7.5 \times 10^6$ cells or c.e. extract. The patient need not be immunized to hapten prior to vaccine administration.

The vaccine composition of the present invention may comprise tumor cells and/or tumor cell extracts. The tumor cells for use in the present invention may be prepared as follows. Tumor masses are processed as described by Berd et al. (1986), supra, incorporated herein by reference in its entirety. The cells are extracted by enzymatic dissociation with collagenase and DNAse by mechanical dissociation, frozen in a controlled rate freezer, and stored in liquid nitrogen until needed. On the day that a patient is to be skin tested or treated, the cells are thawed, washed, and irradiated to about 2500 R. They are washed again and then suspended in Hanks balanced salt solution without phenol red. Conjugation of the prepared cells with DNP is performed by the method of Miller and Claman, *J. Immunol.*, 1976, 117, 1519, incorporated herein by reference in its entirety, which involves a 30 minute incubation of tumor cells with DNFB under sterile conditions, followed by washing with sterile saline.

Cancer cells of a patient may be conjugated to a hapten by isolating the membranes and modifying the membranes or by conjugating the cells to a hapten without first isolating the membranes.

A cancer cell membrane may be prepared by isolating membranes from non-modified preparation of cancer cells of a patient. Cells are suspended in about five volumes of about 30 mM sodium bicarbonate buffer with about 1 mM phenyl methyl sulfonyl fluoride and disrupted with a glass homogenizer. Residual intact cells and nuclei are removed by centrifugation at about 1000 g. The membranes are pelleted by centrifugation at 100,000 g for 90 minutes. The membranes are resuspended in about 8% sucrose and frozen at about −80° C. until needed. To a suspension of membranes (about 5,000,000 cell equivalents/ml), about 0.5 ml of 1 mg/ml dinitrofluorobenzene (DNFB) is added for about 30 minutes. Similarly, other haptens such as and not limited to trinitrophenyl and N-iodoacetyl-N,-(S sulfonic 1-naphtyl) ethylene diamine may be used. Excess DNP is removed by dialyzing the membranes against about 0.15 M PBS for about three days. The membranes are pelleted.

Alternatively, the cancer cell extract, the peptide or the membrane, may be prepared by modifying cancer cells of a patient with a hapten such as dinitrophenyl and then preparing membranes therefrom. Cancer cells of a patient are obtained during biopsy and frozen until needed. About 100 mg of DNFB (Sigma Chemical Co., St. Louis, Mo.) was dissolved in about 0.5 ml of 70% ethanol. About 99.5 ml of PBS was added. DNFB concentration should be about 152 mg/0.1 ml. The solution was stirred overnight in a 37° C. water bath. The shelf life of the solution is about 4 weeks. The cells were thawed and the pellet was resuspended in 5×cells/ml in Hanks balanced salt solution. About 0.1 ml DNFB solution was added to each ml of cells and incubated for about 30 minutes at room temperature. Similarly, other haptens such as and not limited to trinitrophenyl, N-iodoacetyl-N'-(5-sulfonic 1-naphthyl)ethylene diamine, trinitrobenzenesulfonic acid, fluorescein isothiocyanate, arsenic acid benzene isothiocyanate, trinitrobenzenesulfonic acid, sulfanilic acid, arsanilic acid, dinitrobenzene-S-mustard and combinations thereof may be used. The cells were then washed twice in Hanks balanced salt solution. Cells are suspended in about five volumes of about 30 mM sodium bicarbonate buffer with about 1 mM phenyl methyl sulfonyl fluoride and disrupted with a glass homogenizer. Residual intact cells and nuclei are removed by centrifugation at about 1000 g. The membranes are pelleted by centrifugation at 100,000 g for 90 minutes. The membranes are resuspended in about 8% sucrose and frozen at about −80° C. until needed.

From the DNP modified cells, peptide may be extracted, some of which are DNP modified as a result of modifying the cells. Protein extraction techniques, known to those of skill in the art, may be followed by antigen assays to isolate antigen(s) effective for patient treatment. The methods of isolating cell extracts are readily known to those skilled in the art. Briefly, cancerous cells are isolated from a tumor and cultured in vitro. Dinitrophenyl is added to the cultured cells in accordance with the method set forth above. Peptides are isolated from cells according to an established technique of Rotzschke et al., *Nature*, 1990, 348, 252, the disclosure of which is hereby: incorporated by reference in its entirety. The cells are treated with a weak acid. Then they are centrifuged and the supernatants are saved. Fractions containing small peptides are obtained by HPLC, concentrated, and frozen. The fractions are screened for immunological activity by allowing them to bind to autologous B lymphoblastoid cells which are then tested for ability to stimulate melanoma-specific T lymphocytes.

The cells are treated with a weak acid, such as and not limited to trifluoroacetic acid MA). The cells are then centrifuged and the supernatant is saved. Compounds having a molecular weight greater than 5,000 were removed from the supernatant by gel filtration (G25 Sepharose, Pharmacia). The remainder of the supernatant is separated on a reversedphase HPLC column (Superpac Pep S, Pharmacia LKB) in 0.1% trifluoroacetic acid (TFA) using a gradient of increasing acetonitrile concentration; flow rate=1 ml/min, fraction size=1 ml. Fractions containing small peptides are obtained by HPLC according to the method of Sambrook et al., *Molecular Cloning: A Laboratory Manual*, 2nd ed., Cold Spring Harbor Laboratory Press, Cold Spring Harbor, N.Y. (1989), concentrated, and frozen. The fractions are screened for immunological activity by allowing them to bind to autologous B lymphoblastoid cells which are then tested for ability to stimulate tumor- (e.g. melanoma) specific T lymphocytes.

Epstein barr virus (EBV, ATCC CRL-1612, B95-8 EBV transformed leukocytes, cotton top marmoset, *Saguinus oedipus*) is added to B lymphoblastoid cells in culture. The B lymphoblastoid cells are transformed into a B cell tumor from the patient's own lymphocytes. Melanoma from a metastasis is cultured in RPMI 1640+10% fetal calf serum or 10% pooled human serum. The non-adhered cells are washed off with RPMI medium. When the cells are confluent, they are detached with 0.1% EDTA and split into two flasks. This process continues where the confluent cells are continuously split. To test for gamma interferon production by T cells, lymphocytes from a patient's blood are obtained. The patient's own tumor cells, which have been modified with a hapten, such as DNP, are mixed with the lymphocytes to stimulate the T cells. Every seven days, interleukin-2 is added. The T cells are expanded by splitting as disclosed above. The T cells are then restimulated by the hapten modified cells. An enriched population of T cells result which are responsive to the hapten modified cells.

Human cancer vaccines have been developed and tested by a number of workers. Although they can sometimes induce weak immunity to a patient's cancer, they rarely cause tumor regression. The development of inflammatory responses in metastatic tumors was surprisingly found with the DNP-vaccine of the present invention. The tumor becomes reddened, warm and tender. Ultimately, in some cases, the tumor regresses to the extent that the tumor disappears, to the naked eye and microscopically. Microscopically, infiltration of T lymphocytes—into the tumor mass is observed. Therefore, this approach, which increases the inflammatory response and the number and capacity of lymphocytes entering the tumor, is a significant advance in the art.

The effectiveness of the vaccine may be improved by adding various biological response modifiers. These agents work by directly or indirectly stimulating the immune response. Biological response modifiers of the present invention include and are not limited to interleukin-12 and gamma interferon. In this embodiment, IL12 will be given following the each vaccine injection. Administration of IL12 to patients with inflammatory responses is believed to cause the T lymphocytes within the tumor mass to proliferate and become more active. The increased T cell numbers and functional capacity leads to immunological destruction of the tumors. Dosages for IL12 will be prepared in accordance with the dosage indications set forth above.

Patients with metastatic melanoma were treated using an immunotherapy regimen with the following components: 1) vaccine consisting of autologous tumor cells conjugated to DNP; and 2) low dose cyclophosphamide pretreatment. Patients were evaluated to determine whether tumor regression had occurred, to monitor tumor inflammatory responses, and to measure delayed type hypersensitivity to autologous melanoma cells, DNFB (the form of DNP used for skin sensitization), DNP-conjugated autologous lymphocytes, diluent (Hanks solution), purified protein derivative (PPD), and recall antigens (candida, trichophyton, and mumps). Patients who are considered to be deriving benefit (clinical or immunological) from the therapy are continued in the immunotherapy regimen. Subsequent vaccines may be given without cyclophosphamide. In a similar experiment, Interleukin 2 linked to polyethylene glycol was found to not be effective.

In another embodiment, a vaccine comprising chemical extracts of cancer cells conjugated to a hapten and mixed with an immunological adjuvant, such as Bacillus Calmette-Guerin, BCG, is used.

In the present invention, biopsies from human melanoma metastases were examined for expression of cytokine mRNA using RT-PCR. mRNA for IFNγ is found in post-DNP vaccine, inflamed metastases, but only rarely in pre-treatment metastases, even those containing large numbers of residual lymph node lymphocytes. Moreover, the Type II cytokine, IL10, is found in almost all melanoma metastases and appears to be produced by the melanoma cells themselves.

Patients with metastatic melanoma treated with an autologous, DNP-modified vaccine develop inflammatory responses at tumor sites. Histologically, these inflamed lesions are characterized by T cell infiltration which is sometimes associated with tumor cell destruction. In the present invention, biopsy specimens of 8 subcutaneous metastases that had developed inflammation following vaccine treatment were tested for expression of mRNA for IFNγ, IL4, TNF, and IL10. Post-vaccine, inflamed biopsies contained mRNA for IFNγ (5/8), IL4 (4/8) or both (3/8), and for TNF (4/7). In contrast, IFNγ mRNA was detected in only 1/17 and TNF mRNA in 2/16 control specimens (pre-treatment lymph node metastases or non-inflamed subcutaneous metastases). mRNA for IL10, a cytokine with anti-inflammatory properties, was detected in 24/25 melanoma metastases and was independent of lymphoid content; in situ PCR confirmed that melanoma cells were the major source. These findings provide a new parameter by which to measure the effects of cancer immunotherapy.

The present invention is aimed at analyzing freshly obtained metastatic melanoma biopsies for the presence of cytokine mRNA which correlates with a productive immune response at the tumor site. The expression of IFNγ or IL4 mRNA is characteristic of melanoma metastases that have developed an inflammatory response following administration of DNP-modified autologous vaccine. on the other hand, expression of IL10 mRNA is independent of an inflammatory response and seen in nearly all melanoma biopsy specimens. Examination of cell lines derived from melanoma biopsies as well as in situ PCR analysis demonstrated that the source of IL10 is melanoma cells themselves rather than the associated lymphocytes.

Perhaps the most important finding of this work is the negative one: mRNA for IFNγ and IL4 generally is not found in melanoma metastases from untreated patients, nor in metastatic masses that contain large numbers of lymph node lymphocytes. This provides a low background activity of in situ cytokine production against which to compete melanoma tissues whose T cell population has been altered by immunotherapy. Moreover, it underscores an important biological point: T cells extracted from melanoma nodal metastases probably represent the residua of the original lymph node population rather than lymphocytes that have actually infiltrated the tumor as a result of their recognition of melanoma antigens. Since they are not antigen-activated, they have received no stimulus to produce IFNγ or IL4.

In contrast, biopsy specimens obtained following administration of DNP-vaccine typically expressed mRNA for IFNγ. However, DNP-vaccine-induced inflammatory responses cannot be characterized as Type I since some of these samples contained IL4 as well. Given the sensitivity of PCR-based mRNA analysis, such a pattern could be produced by a small focus of IL4-producing T cells in the midst of a T cell infiltrate that is predominantly IFNγ-producing. On the other hand, the presence of mRNA for IFNγ and IL4 could signify the presence of T cells that produce both cytokines—so-called $TH_O$ cells (Lee et al, *Eur. J. Immunol.* 1992 22:1455–1459). Resolution of this issue will require analyses that allow correlation of mRNA expression with morphology, such as in situ PCR. Whatever the results, these findings suggest that intra-tumor cytokine production may be an important parameter to measure in patients undergoing immunotherapy.

The present invention strongly suggest that the source of IL10 mRNA is the melanoma cells themselves, rather than the associated lymphocytes. Strong IL10 mRNA bands were detected in 24/25 biopsies, and its expression was independent of the number of associated lymphocytes or the presence of DNP-vaccine-induced inflammation. Moreover, in situ PCR clearly showed IL10 mRNA within melanoma cells. Cell lines derived from the biopsy material expressed IL10 mRNA and produced IL10 as measured by ELISA.

The physiologic significance of IL10 production in melanoma tissues is not clear. IL10 is known to be an antiinflammatory cytokine with ability to inhibit T cell proliferation and IL2 production (Jinquan, T., et al., *J. Immunol.* 1993 151:4545–4551) and delayed type hypersensitivity (Lee, supra), probably by reducing macro phage costimulatory function. Thus IL10 could suppress the activation and proliferation of melanoma-reactive T cells that have infiltrated the tumor site. However, IL10 recently has been shown to be a chemoattractant for CD8+ T cells (Jinquan, supra); this property could account for the predominance of CD8+ cells in DNP-vaccine-induced lymphoid infiltrates. In either case, modulation of IL10 production at the tumor site may have important consequences for the tumor-host relationship.

The scope of the present invention also includes a method of screening for cytokine production by a tumor to determine the efficacy of an autologous, irradiated hapten conjugated cell composition in a patient suspected of having cancer, said method comprising administering said hapten conjugated composition to said patient; obtaining a sample comprising nucleic acids from a patient tissue sample; amplifying nucleic acids specific for a cytokine or amplifying a signal generated by hybridization of a probe specific to a cytokine specific nucleic acid in said tissue sample; and detecting the presence of the amplified nucleic acids or the amplified signal wherein the presence of amplified nucleic acids or amplified signal indicates cancer, wherein the presence of amplified nucleic acids or amplified signal from said patient tissue sample indicates efficacy of said hapten conjugated composition.

The tissue sample may be a malignant or premalignant tumor, a melanoma tumor for example, or a subcutaneous inflammatory metastatic melanoma, for example. In addition, a tissue sample may be a solid or liquid tissue sample such as and not limited to all or part of a tumor, saliva, sputum, mucus, bone marrow, serum, blood, urine, lymph, or a tear from a patient suspected of having cancer.

Nucleic acids, such as DNA (including cDNA) and RNA (including mRNA), are obtained from the patient tissue sample. Preferably RNA is obtained from a tissue sample. Total RNA is extracted by any method known in the art such as described in Sambrook et al., *Molecular Cloning: A Laboratory Manual* (Cold Spring Harbor Laboratory, Cold Spring Harbor, N.Y., 1989), incorporated herein by reference in its entirety.

Nucleic acid extraction is followed by amplification of the same by any technique known in the art. The amplification step includes the use of at least one primer sequence which is complementary to a portion of a cytokine specific sequence. Cytokine specific sequences are defined for purposes of the present invention to include (and are not limited to) all or part of sequences which encode IFNγ, TNF, IL-2, IL-12, and IL-13. Generally, the primer sequence is about 21 nucleotides to about 33 nucleotides, preferably about 21 nucleotides, about 31 nucleotides, 32 nucleotides, and about 33 nucleotides in length.

Primer sequences useful in the amplification methods include and are not limited to β actin, SEQ ID NOS: 1 and 2; IFNγ, SEQ ID NOS: 3 and 4; IL4, SEQ ID NOS: 5 and 6; IL10 , SEQ ID NOS: 7 and 8; and TNF, SEQ ID NOS: 9 and 10.

Where a template dependent process of amplification uses a pair of primers, one primer of the pair may comprise oligonucleotides which are complementary to nucleic acid sequences which encode cytokine specific proteins. The one primer of the pair may be selected from the group consisting of SEQ ID NOS: 1 to 10.

Alternatively, each of the two oligonucleotides in the primer pair may be specific to a nucleic acid sequence which encodes a cytokine. The primers may be designed to be complementary to separate regions of a cytokine sequence for example. By separate regions is meant that a first primer is complementary to a 31 region of a cytokine sequence and a second primer is complementary to a 5' region of a cytokine sequence. Preferably, the primers are complementary to distinct, separate regions and are not complementary to each other. The primers of SEQ ID NOS: 1–10 are merely exemplary of the primers which may be useful in the present invention.

When an amplification method includes the use of two primers, such as the polymerase chain reaction, the first primer may be selected from the group consisting of SEQUENCE ID NOS: 1, 3, 5, 7, and 9, and the second primer may be selected from the group consisting of SEQUENCE ID NOS: 2, 4, 6, 8, and 10. Any primer pairs which transcribe nucleic acids toward each other and which are specific for cytokines may be used in accordance with the methods of the present invention.

Total extraction of RNA is preferably carried out. As used herein, the term "amplification" refers to template-dependent processes and vector-mediated propagation which result in an increase in the concentration of a specific nucleic acid molecule relative to its initial concentration, or in an increase in the concentration of a detectable signal. As used herein, the term template-dependent process is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, J. D. et al., In: *Molecular Biology of the Gene,* 4th Ed., W. A. Benjamin, Inc., Menlo Park, Calif. (1987) incorporated herein by reference in its entirety). Typically, vector mediated methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., Molecular Cloning (A Laboratory Manual), Cold Spring Harbor Laboratory, 1982, each incorporated herein by reference in its entirety.

A number of template dependent processes are available to amplify the target sequences of interest present in a sample. one of the best known amplification methods is the polymerase chain reaction (PCR) which is described in detail in U.S. Pat. Nos. 4,683,195, 4,683,202 and 4,800,159, and in Innis et al., *PCR Protocols,* Academic Press, Inc., San Diego Calif., 1990, each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended,primers will dissociate from the target to form reaction products, excess primers will bind to the target and to the reaction products and the process is repeated. Preferably a reverse transcriptase PCR amplification procedure may be performed in order to quantify the amount of mRNA amplified. Polymerase chain reaction methodologies are well known in the art.

Another method for amplification is the ligase chain reaction (referred to as LCR), disclosed in EPA No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Application No. PCT/US87/00880, incorporated herein by reference in its. entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha -thio] triphosphates in one strand of a restriction site (Walker, G. T., et al., *Proc. Natl. Acad, Sci.* (U.S.A.) 1992, 89:392–396, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and involves annealing several probes throughout a region targeted for amplification, followed by a repair reaction in which only two of the four bases are present. The other two bases can be added as biotinylated derivatives for easy detection. A similar approach is used in SDA.

Cytokine specific sequences can also be detected using a cyclic probe reaction (CPR). In CPR, a probe having a 31 and 51 sequences of non-cytokine specific DNA and middle sequence of cytokine specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a cytokine specific nucleic acid.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS) (Kwoh D., et al., *Proc. Natl. Acad. Sci. (U.S.A.)* 1989, 86:1173, Gingeras T. R., et al., PCT Application WO 88/10315, incorporated herein by reference in their entirety), including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has prostate specific sequences. Following polymerization, DNA/RNA hybrids are digested with RNase H while double stranded DNA molecules are heat denatured again. In either case the single stranded DNA is made fully double stranded by addition of second prostate specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate prostate cancer specific sequences.

Davey, C., et al., European Patent Application Publication No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT Application WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., In: *PCR Protocols: A Guide to Methods and Applications* 1990, Academic Press, N.Y.) and one-sided PCR11 (Ohara, O., et al., Proc. Natl. Acad. Sci. (U.S.A.) 1989, 86:5673–5677), all references herein incorporated by reference in their entirety.

Methods based on ligation of two (or more) oligonucleotides in the presence of nucleic acid having the sequence of the resulting "di-oligonucleotide", thereby amplifying the di-oligonucleotide (Wu, D. Y. et al., *Genomics* 1989, 4:560, incorporated herein by reference in its entirety), may also be used in the amplification step of the present invention.

Following amplification, the presence or absence of the amplification product may be detected. The amplified product may be sequenced by any method known in the art, including and not limited to the Maxam and Gilbert method, see Sambrook, supra. The sequenced amplified product may then be compared to results obtained with tissue excised prior to vaccine treatment. Tissue samples obtained prior to vaccine treatment should be free of cytokine sequences, particularly IFNγ, TNF, IL2, IL12, and IL13. The nucleic acids may be fragmented into varying sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labelled probe is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 200 nucleotides in length. Mismatches such as and not limited to sequences with similar hydrophobicity and hydrophilicity, will be known to those of skill in the art once armed with the present disclosure. Various labels for visualization or detection are known to those of skill in the art, such as and not limited to fluorescent staining, ethidium bromide staining for example, avidin/biotin, radioactive labeling such as $^{32}$P labeling, and the like. Preferably, the product, such as the PCR product, may be run on an agarose gel and visualized using a stain such as ethidium bromide. See Sambrook et al., supra. The matrix may then be analyzed by autoradiography to locate particular fragments which hybridize to the probe.

A diagnostic kit for screening for the efficacy of an autologous, irradiated, hapten conjugated cell composition comprising in one or more containers, a pair of primers, wherein one of the primers within said pair is complementary to a cytokine specific sequence, wherein said primer is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, and a means for visualizing amplified DNA; said kit useful for determining the efficacy of said composition.

The invention is further illustrated by means of the following actual examples 1–8 and 11 and prophetic examples 9–10 and 12–14 which are meant to be illustrations only and are not intended to limit the present invention to these specific embodiments.

EXAMPLE 1

Sixty-four patients were treated with metastatic melanoma using a melanoma vaccine, prepared in accordance with the methods set forth above, preceded by low dose cyclophosphamide (CY) and monitored for immunological effects and anti-tumor activity. On day 0, the patients were given cyclophosphamide 300 Mg/M$^2$ i.v. Three days later, they were injected intradermally with vaccine consisting of $10 \times 10^6$ to $25 \times 10^6$ autologous, cryopreserved, irradiated (2500 R) tumor cells mixed with BCG; the tumor cells were obtained by dissociation of metastatic masses enzymatically (collagenase and DNAse). This treatment sequence was repeated every 28 days for 8 treatments.

The toxicity of the therapy was limited to a local inflammatory response at the injection site and mild nausea and vomiting following cyclophosphamide administration. There were 40 evaluable patients with measurable metastases; 5 had responses—4 complete and 1 partial. The median duration of response was 10 months (7–84+ months). One patient continues to be in remission at 11 years. Regression occurred not only in skin and nodal metastases, but also in lung and liver metastases. In 6 additional patients, an anti-tumor response was observed that seemed peculiar to this vaccine therapy, i.e., the regression of metastatic lesions that appeared after the immunotherapy was begun. In 3 patients this "delayed" regression occurred in two or more tumors.

Delayed-type hypersensitivity (DTH) to autologous, mechanically-dissociated melanoma cells was detectable in only 16% of patients before treatment, as compared with in 46%, 56% and 73% of patients on days 49, 161 and 217, respectively. The increases in delayed type hypersensitivity following immunotherapy were statistically significant by a non-independent t-test; day 0 vs. day 49, p<0.001; day 0 vs. day 161, p<0.001; day 0 vs. day 217, p=0.021. Overall, 26/43 patients (61%) exhibited a positive delayed type hypersensitivity response ($\geq 5$ mm) to autologous melanoma cells at some time point. Patients also developed strong delayed type hypersensitivity to the enzymes used to prepare the tumor cell suspensions: of 24 patients tested for delayed type hypersensitivity with a mixture of collagenase and DNase (each at 1 Mg/ml) after two vaccine treatments, 21 (88%) had responses>5 mm. Antitumor responses to the vaccine were strongly associated with delayed type hypersensitivity to mechanically-dissociated, autologous melanoma cells, as indicated by three observations: 1) 8/10 patients who exhibited tumor regression had positive delayed type hypersensitivity; 2) in post-surgical adjuvant patients, there was a highly significant correlation between the intensity of delayed type hypersensitivity to autologous melanoma cells and the time to recurrence of tumor (r=0.680, p<0.001); 3) nine patients who developed delayed type hypersensitivity to the autologous melanoma cells in their original vaccine ("old" tumor) developed new metastases ("new" tumor) that did not elicit delayed type hypersensitivity or elicited a much smaller response. The patients were compared to their condition prior to treatment with the vaccine. The patients treated prior to the vaccine study were removed from treatment one to two months prior to starting the vaccine study. Accordingly, the patients were untreated beginning the vaccine study.

In three cases we were able to excise regressing tumors for histological examination; such tumors were characterized by an intense infiltration of lymphocytes. In contrast, tumors excised from these patients before immunotherapy consisted of homogeneous masses of malignant cells without significant lymphocytic infiltration.

This study shows that the use of cyclophosphamide allows the development of an immune response to melanoma-associated antigens in cancer-bearing patients.

EXAMPLE 2

Patients with metastatic melanoma were sensitized to DNP by topical application to the upper arm with 1% dinitrochlorobenzene (DNCB) or dinitrofluorobenzene (DNFB). Two weeks later they were injected with a vaccine consisting of $10 \times 10^6$ to $25 \times 10^6$ autologous, irradiated melanoma cells conjugated to DNP and mixed with BCG. Cyclophosphamide 300 mg/M$^2$i.v. was given 3 days before DNCB (or DNFB) or vaccine. Of 4 evaluable patients, 3 have developed a striking inflammatory response in tumor masses after 2 vaccine treatments (8 weeks). Patient #1 developed erythema and swelling in the >50 large (1–3 cm) dermal metastases on her leg and lower abdomen, followed by ulceration and drainage of necrotic material, and some are beginning to regress. Biopsy showed infiltration with CD4+ CD8+ T lymphocytes. Patient #2 developed erythema and swelling in the skin of her lower abdomen and groin overlying large (8 cm) nodal masses. These have not yet regressed, but have changed in consistency from rockhard to fluctuant. Patient #3 exhibited moderate erythema in the skin overlying 3 subcutaneous metastases. All 3 patients have developed delayed type hypersensitivity to both DNCB and to DNP conjugated autologous lymphocytes. The patients were compared to their condition prior to treatment with the vaccine. The patients treated prior to the vaccine study were removed from treatment one to two months prior to starting the vaccine study. Accordingly, the patients were untreated beginning the vaccine study.

EXAMPLE 3

Fifteen patients (including 3 patients from Example 2) were treated with metastatic melanoma using a novel form of immunotherapy, i.e., tumor cell vaccine conjugated to DNP. Patients were sensitized to DNP by topical application to the upper arm with 5-dinitrochlorobenzene. Then every 4 weeks they received cyclophosphamide 300 Mg/M$^2$ followed 3 days later by injection of $10 \times 10^6$ to $25 \times 10^6$ autologous, irradiated melanoma cells conjugated to DNP. Patients received 6–8 treatments. Most patients (92%) developed delayed-type hypersensitivity (DTH) to DNP-conjugated autologous lymphocytes or tumor cells (mean DTH=17 mm). The vaccine induced a striking inflammatory response in subcutaneous and nodal metastases in 11/15 patients, consisting of erythema, swelling, warmth, and tenderness around tumor masses, and, in one case, purulent drainage. Biopsies showed infiltration with lymphocytes, which, by immunopathological and flow cytometric analyses, were mainly CD3+, CD4−, CD8+, HLA-DR+ T cells. The melanoma cells in these tissues strongly expressed ICAM-1, which serves as an adhesion molecule for T cells. Thus, DNP-vaccine seems to induce a degree of antimelanoma immunity not seen with previously tested immunotherapy. The patients were compared to their condition prior to treatment with the vaccine. The patients treated prior to the vaccine study were removed from treatment one to two months prior to starting the vaccine study. Accordingly, the patients were untreated beginning the vaccine study.

EXAMPLE 4

This example examined the therapeutic effects of DNP-vaccine in patients with surgically-resected metastases and no clinical evidence of metastatic disease. Forty seven patients were sensitized to the hapten, DNFB (dinitrofluorobenzene). Then they were treated by intradermal injection of autologous, irradiated melanoma cells conjugated to DNP. Additional vaccine injections were administered every 28 days for a total of eight treatments. All patients were periodically tested for Delayed Type Hypersensitivity, DTH, responses to autologous melanoma cells, DNP-conjugated autologous lymphocytes, and microbial antigens. In vitro studies were performed with cryopreserved lymphocytes extracted from metastatic tumors and/or separated from peripheral blood.

DNP-VACCINE THERAPY OF MELANOMA

| DAY OF WEEK | M | W | F | M | T | M | W | TH | M | TH | M | W | M |
|---|---|---|---|---|---|---|---|---|---|---|---|---|---|
| DAY OF STUDY | −21 | −19 | −17 | −14 | −13 | 0 | 2 | 3 | 28 | 31 | 49 | 51 | 56 |
| CYCLO PHOSPH AMIDE | | X | | | | X | | X | | | | | REPEAT |
| DNP VACCINE | | | | | | | | | X | | X | | CYCLE |
| DNFB SENS | | | | X | X | | | | | | | | FOR |
| DNFB CHALL | | | | | | | X | | | | | | A |
| APPLY SKIN TESTS | X | | | | | X | | | | | X | | TOTAL |
| READ SKIN TESTS | | X | | | | | | X | | | | X | OF |
| OBTAIN PBL | X | | | | | X | | | | | X | | 8 |
| OBTAIN SERUM | X | | | | | X | | | | | X | | VACCINES |
| ROUTINE LABS | X | | | | | | | | | | X | | |

CY (cyclophosphamide) = 300 mg/M² i.v. bolus only before first two vaccines
VACCINE = 5 × 10⁶ to 20 × 10⁶ autologous, irradiated melanoma cells mixed with BCG
DNFB SENS = 1.0 mg in 0.1 ml acetone-corn-oil applied to ventral upper arm
DNFB CHALL = 200 μg in 0.1 ml acetone-corn-oil applied to forearm
APPLY SKIN TESTS = autologous melanoma cells, peripheral blood lymphocytes (PBL), peripheral blood lymphocytes conjugated to DNP (PBL-DNP), purified protein derivative (PPD) (skin test for tuberculosis), microbial recall antigens
*Day 0: PBL, PBL-DNP only
READ SKIN TESTS = mean diameter of induration
OBTAIN PBL = 100 cc heparinized blood
ROUTINE LABS = complete blood count (CBC), differential blood count (diff), platelet count (platelets), SMA-12 (panel of routine lab tests, blood urea nitrogen (BUN)

patients were sensitized to the hapten, DNFB (dinitrofluorobenzene). Then they were treated by intradermal injection of autologous, irradiated melanoma cells conjugated to DNP. Additional vaccine injections were administered every 28 days for a total of eight treatments. All patients were periodically tested for Delayed Type Hypersensitivity, DTH, responses to autologous melanoma cells, DNP-conjugated autologous lymphocytes, and microbial antigens. In vitro studies were performed with cryopreserved lymphocytes extracted from metastatic tumors and/or separated from peripheral blood.

Figure 12:
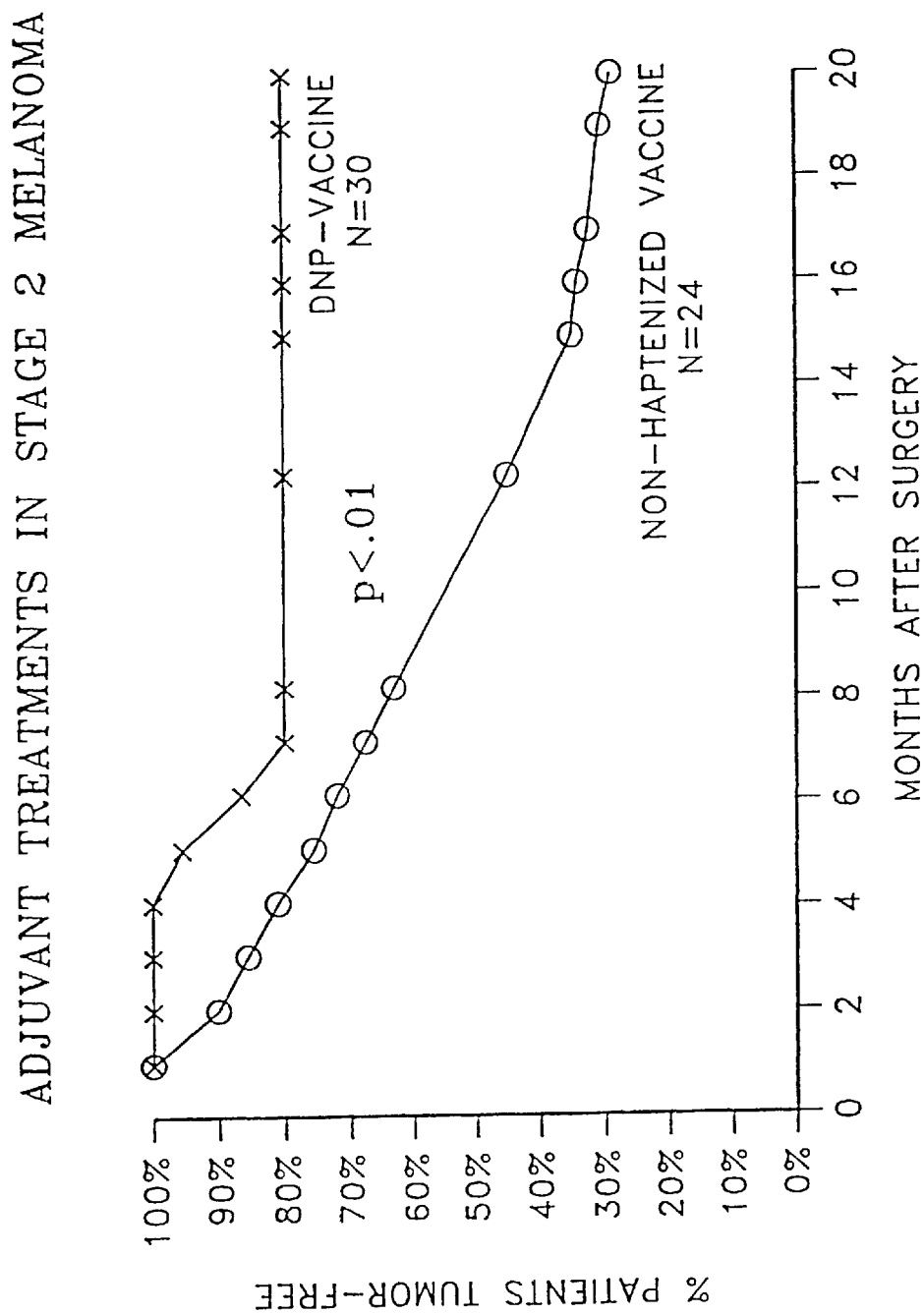
FIG. 12 displays a graph of the percentage of patients tumor free in the months following surgery treated with DNP vaccine and non-haptenized control vaccine.

The graph of FIG. 12 compares the percent of patients tumor free in the months following surgery treated with DNP vaccine and non-haptenized control vaccine. The study examined the therapeutic effects of DNP-vaccine in patients with surgically-resected metastases and no clinical evidence of metastatic disease. All patients were sensitized to the hapten, DNFB (dinitrofluorobenzene). Then they were treated by intradermal injection of autologous, irradiated melanoma cells conjugated to DNP. Additional vaccine injections were administered every 28 days for a total of eight treatments. All patients were periodically tested for Delayed Type Hypersensitivity, DTH, responses to autologous melanoma cells, DNP-conjugated autologous lymphocytes, and microbial antigens. In vitro studies were performed with cryopreserved lymphocytes extracted from metastatic tumors and/or separated from peripheral blood.

Sensitization to DNP—Patients initially were sensitized to DNP as follows: On day −17, cyclophosphamide, 300 Mg/M² was administered as a rapid i.v. infusion. Three days later, on days −14 and −15, patients were sensitized with DNFB (dinitrofluorobenzene): 1 mg DNFB dissolved in acetone-corn oil and applied topically in a volume of 0.1 ml within the confines of a 2 cm diameter steel ring. Two weeks later, patients were tested for reactivity to DNP by topical application of 200 pg DNFB and intradermal injection of DNP-conjugated autologous PBL. Cyclophosphamide was reconstituted in sterile water and the proper dosage was administered by rapid i.v. infusion.

Vaccine Preparation—Tumor masses were processed. Cells were extracted by enzymatic dissociation with collagenase and DNAse and by mechanical dissociation, frozen in a controlled rate freezer, and stored in liquid nitrogen until needed. On the day that a patient was to be treated, the cells were thawed, washed, and irradiated to 2500 R. Then they were washed again and suspended in Hanks balanced salt solution without phenol red.

Conjugation of melanoma cells with DNP was performed. This involved a 30 minute incubation of tumor cells with dinitrofluorobenzene (DNFB) under sterile conditions, followed by washing with sterile saline.

The vaccine consists of 5–20×10$^6$ live tumor cells suspended in 0.2 ml Hanks solution. When BCG is added, it consisted of 0.1 ml of a 1:10 dilution of Tice BCG. Each vaccine treatment consisted of three injections into contiguous sites on the upper arms or legs, excluding limbs ipsilateral to a lymph node dissection.

Study Procedure—On day 0, patients received cyclophosphamide 300 Mg/M$^2$ as a rapid i.v. infusion. Three days later, on day +3, they were injected intradermally with autologous melanoma vaccine. Additional vaccine injections were administered every four weeks for a total of eight treatments. Cyclophosphamide was given only prior to the first two injections. All vaccines were DNP-conjugated and mixed with Bacillus Calmette-Guerin (BCG). BCG is the Tice strain (substrain of the Pasteur Institute strain) obtained from Organon Teknika Corporation, Durham, N.C. The freeze-dried material was reconstituted with 1 ml sterile water and diluted 1:10 in phosphate-buffered saline, pH 7.2; then 0.1 ml was drawn up, mixed with the vaccine and injected. All vaccines were injected into the same site (upper arm or leg).

Immunological evaluation—Skin-testing was performed by the intradermal injection of 0.1 ml of test material on the forearm, and delayed type hypersensitivity was assessed at 48 hours by measuring the mean diameter of induration. Positive reactions were photographed. The following materials were tested: 1) 1×10$^6$ irradiated autologous melanoma cells; 2) 3×10$^6$ autologous peripheral blood lymphocytes, both unconjugated and conjugated to DNP; 3) Hanks solution; 4) PPD-intermediate strength; and 5) microbial recall antigens—Candida, trichophyton, and mumps. Also, contact sensitivity to DNFB was tested by applying 200 $\mu$g to the skin of the forearm and examining the area for a circle of induration at 48 hours.

All patients had blood collected for separation and cryopreservation of lymphocytes and serum each time skin-testing was performed (see Table 1 for schedule of blood drawing). Periodically, these were tested for: 1) proliferative and cytotoxic response to autologous melanoma cells; and 2) proliferative response to DNP-conjugated autologous lymphocytes.

Duration of Study

1) Patients were treated with eight courses of vaccine which required about eight months. Treatment was then stopped. These patients will be monitored until at least five years has elapsed since their initial surgery.

2) Patients who developed regional recurrence or distant metastases before the completion of eight treatments were taken off the study and treated as clinically indicated (chemotherapy or surgery).

The control group consisted of 22 patients with melanoma metastatic to regional lymph nodes. They underwent surgical resection of their disease, at which time they had no clinical evidence of metastatic melanoma. Then, they received treatment with a non-haptenized, autologous melanoma vaccine. First, they were given cyclophosphamide, 300 Mg/M$^2$. Three days later they were injected intradermally with the vaccine, which consisted of 10×10$^6$ to 25×10$^6$ irradiated, autologous melanoma cells mixed with BCG. The cyclophosphamide-vaccine treatment was repeated every 28 days. A total of eight treatments was given. The patients were clinically evaluated every two months.

Only 20% of the control patients were cancer-free at two years. In contrast, patients treated with the DNP-vaccine of the invention had significantly higher cancer-free survival as set forth above.

The patients who received haptenized vaccine all had melanoma metastatic to regional lymph nodes, but no evidence of distant metastases. Patients in this condition are routinely treated by surgical resection of the diseased nodes. Surgical resection renders them clinically disease-free, but they have an 80–85% chance of developing metastatic melanoma with two years.

The patients in the control group were in the same clinical condition in order to be comparable to the haptenized vaccine group. Thus, the control group also consisted of patients with melanoma metastatic to regional lymph nodes, but no evidence of distant metastases, who had undergone surgical resection of the diseased nodes. when treatment was initiated with the non-haptenized vaccine, the control patients were clinically disease-free, but as previously noted, 80% developed distant metastases.

Patients with surgically incurable melanoma were not selected as controls because such patients have a cure rate approaching zero, and an even shorter survival than patients with resectable lymph node metastases. Moreover, it is not possible in such patients to measure disease-free survival, a parameter that was dramatically prolonged by the vaccine of the present invention.

A statistical analysis of the data was performed as follows: Kaplan-Meir plots of disease-free survival and total survival were constructed. The difference between DNP-vaccine patients and control patients was analyzed by the Mantel log-rank test. These are standard statistical methods for analyzing such data. The difference was highly significant with $p<0.01$.

Seventeen patients additional were subsequently treated according to the protocol outlined above (the size of the control group was not increased for, reasons set forth above). The results maintained statistically significant differences in disease-free survival and total survival.

EXAMPLE 5

Administration of an autologous, dinitrophenyl (DNPL-conjugated melanoma vaccine induces T cell infiltration of metastatic tumors, and prolongs survival of patients who have undergone lymphadenectomy for bulky regional metastases. These effects appear to be due to melanoma-specific T cells. Their generation is contingent upon T cells with specificity for DNP-modified melanoma cells (DNP-MEL).

Clinical Protocol

All patients had metastatic melanoma and were undergoing immunotherapy with autologous, DNP-conjugated tumor vaccine, as previously described in Berd, D., et al., Cancer Res., 1991, 51, 273 I, incorporated here in by reference in its entirety. Informed consent was obtained from the patients. Patients were pre-treated with cylophosphamide 300 mg/M$^2$, see Berd et al. (1986) supra, and three days later were sensitized to DNFB by topical application of 0.1 ml of a 1 DNFB solution in acetone-corn oil on two consecutive days. Two weeks later patients were again given cyclophosphamide, followed 3 days later by injection of DNP-conjugated melanoma vaccine. DNP-vaccine was repeated every 28 days. Cyclophosphamide was given prior to the first two cycles. The vaccine consisted of $10 \times 10^6 - 25 \times 10^6$ cryopreserved, autologous, irradiated (2500 R), DNP-conjugated melanoma cells conjugated to DNP mixed with BCG. All tumor preparations contained lymphocytes which were the residua of tumor-infiltrated lymph node tissue. Serum and PBL were collected at the following time points: day 0 (before sensitization), day 14 (2 weeks after DNFB sensitization), day 63 (after 2 vaccines), day 119 (after 4 vaccines), day 175 (after 6 vaccines), and day 231 (after 8 vaccines).

Cellular Reagents

PBL were separated by density gradient centrifugation on Ficoll metrizoate. They were suspended in freezing medium (RPMI-1640 (Mediatech, Washington D.C.)+11 human albumin+10 dimethyl sulfoxide) frozen in a controlled-rate freezer, and stored in liquid nitrogen. HLA typing of PBL was performed by the Thomas Jefferson University Hospital Clinical Laboratory.

Melanoma cells were enzymatically extracted from metastatic masses according to the method of Berd, D., et al., (1986) super, incorporated herein by reference in its entirety, and cryopreserved. Cell lines were derived from these suspensions and were maintained in RPMI-1640 with 10% fetal calf serum. Melanoma cell lines from the patients used in this study were distinguished by MHC class 1 differences determined by flowcytometric analysis with a panel of monoclonal antibodies obtained from the American Type Culture Collection: (HB82=HLA-A2, HB122=HLA-A3, HB164=HLA-A11,24).

Hapten Conjugation

PBL were DNP-modified by a 30 minute incubation with aqueous DNFB or DNBS, according to the methods of Miller, S. D. and H. N. Claman, *J. Immunol.,* 1976, 117, 1519 and Geczy, A. F. and A. Baumgarten, Immunology, 1970, 19, 189, (incorporated herein by reference in their entirety) respectively; the two methods yielded equivalent results. For specificity controls, cells were modified with TNP by incubation with TNBS, or with oxazolone, according to the methods of Fujiwara, H. et al., *J. Immunol.,* 1980, 124, 863 and Boerrigter, G. H. and R. J. Scheper, *J. Invest. Dermatol.,* 1987, 88, 3, (incorporated herein by reference in their entirety) respectively. Hapten conjugation was repeated with melanoma cells.

Delayed-Type Hypersensitivity (DTH)

Cryopreserved PBL were thawed, washed, and resuspended in Hanks balanced salt solution. The cells were divided into three groups: unmodified, conjugated to DNP, and conjugated to TNP. After washing, $1 \times 10^6$ melanoma cells or $3 \times 10^6$ PBL were suspended in 0.1 ml Hanks solution and injected intradermally on the forearm. DTH was determined at 48 hours by measuring the mean diameter of induration. The DTH assay was repeated with melanoma cells.

All patients developed DTH to DNP-modified autologous PBL (FIG. 1). DTH responses were evident two weeks after topical application of DNFB (day 14), and then remained stable throughout the period of monthly vaccine administration. DNP-conjugated autologous melanoma cell suspensions elicited stronger DTH than DNP-PBL (mean SE: PBL=13.3 mm±1.3 mm, melanoma cells=21.9 mm±3.6 mm; p<0.01). DTH was specific for DNP-modified "self", since autologous PBL conjugated to TNP elicited no response in 50 patients tested.

Anti-DNP Antibody

An ELISA was developed by coating microliter wells with DNP-conjugated PBL. This method was found to be preferable to coating plates with DNP-conjugated albumin because it resulted in lower background readings with serum of pre-immunized patients. DNP-conjugated PBL ($5 \times 10^5$ in 0.1 ml) were added to each well of a 96 flat bottom plate. The cells were fixed to the plate by drying followed by a 5 minute exposure to 100% methanol. Then, the plates were washed five times with phosphate buffered saline+0.05% Tween-20. Serial dilutions of test sera were added to the wells and the plate was incubated in a humidified chamber at 37° C. for 1 hour. After the incubation, the plate was washed five times, and then horse radish peroxidase-conjugated goat anti-human immunoglobulin (Cappel Laboratories, Malvern, Pa.) was added at predetermined optimal dilution. For detecting IgG or IgM antibodies, peroxidase-conjugated goat anti-human IgG or IgM were used, respectively. After a 1 hour incubation at 37° C., the plate was washed five times and 0.1 ml of substrate (-phenylenediamine, Sigma Chemical Co., St. Louis, Mo.) was added to each well followed by 50 pl of 0.12 Oi hydrogen peroxide. The plate was read in an ELISA plate reader.

The assay was validated using a murine anti-DNP monoclonal antibody (clone SPE-7; Sigma ImmunoChemicals) and a peroxidase-conjugated antimouse immunoglobulin antibody as the second step reagent. Subsequently, the positive control consisted of a serum sample from a patient who had received multiple injections of DNP-vaccine. Anti-DNP antibody titer of each serum sample was defined as follows: (peak OD of sample)×(reciprocal of the dilution having an OD equal to half the peak OD of positive control) Butler, J. E., *Methods Enzymol.,* 1981, 73, 482.

Figure 2:
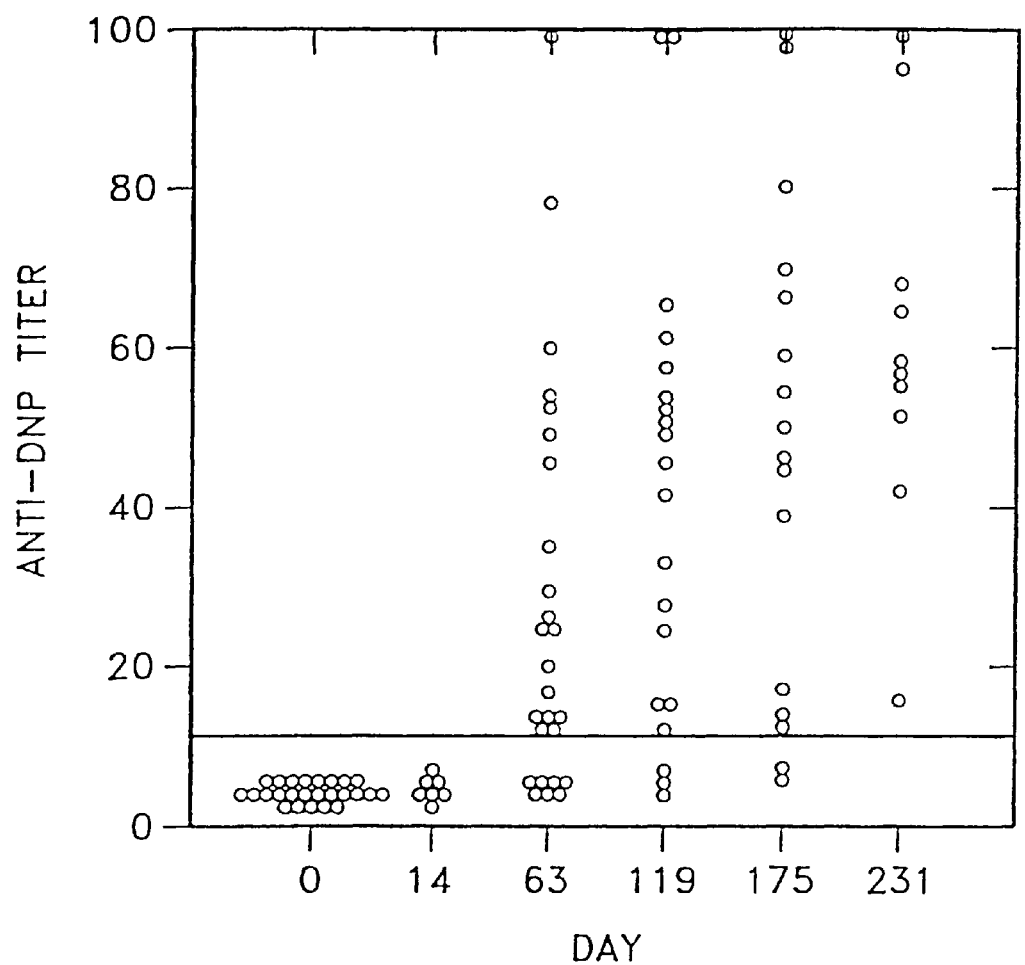
FIG. 2 exhibits antibody response to DNP. Serum obtained at various time points was tested for antibody (total immunoglobulin) to DNP using an ELISA. The titer was defined as: (peak OD of sample)×(reciprocal of the dilution that gave an OD equal to half the peak OD of positive control).

Anti-DNP antibody developed in 24 out of 27 patients tested (FIG. 2). In contrast to DTH, antibody was not induced by DNFB topical application (day 14). In 19 patients, titers increased above pre-immunization levels after two intradermal injections of DNP-conjugated melanoma cells (day 63); in 5 additional patients, significant titers were found only after 4 to 6 vaccines. In all patients, IgG antibody was detected; anti-DNP IgM was found in only three patients. Anti-DNP antibody cross reacted with TNP, shown by binding to TNP-modified cells, but not to the unrelated hapten, oxazolone.

Development of T cell Lines

PBL ($1 \times 10^6$) were mixed with autologous DNP-conjugated B lymphoblastoid cells ($1 \times 10^5$) in 24 well flat bottom plates in lymphocyte culture medium. After 7 days of culture, IL2 100 U/ml (a gift of Cetus Oncology, Emeryville, Calif.) was added. Expanding T cell cultures were maintained in medium+IL2 and were split as needed to maintain a concentration of about $2 \times 10^6$ cells in a 22 mm diameter well. Every 14 days, the cultures were restimulated by adding autologous DNP-conjugated B lymphoblastoid cells. Phenotypes were determined by flow cytometry with a panel of monoclonal antibodies (Becton-Dickinson, San Jose, Calif.). Separation of CD8+ and CD4+T cells was accomplished by indirect panning in which T cells coated with anti-CD8 or anti-CD4 monoclonal antibodies were adhered to antiimmunoglobulin-coated dishes using standard techniques according to the methods of Wysocki, L. J. and V. L. Sato, *Proc. Natl. Acad. Sci. USA,* 1978, 75, 2844, incorporated herein by reference in its entirety; the adherent cells were isolated and expanded with DNP-modified stimulators and IL2.

Phenotypically homogeneous subpopulations of T cells were obtained by culturing at limiting dilution in round-bottom microliter wells in lymphocyte culture medium containing $2 \times 10^5$ irradiated allogeneic feeder cells, 200

U/ml IL2, and phytohemagglutinin. Wells with growing lymphocyte colonies were screened for ability to proliferate in response to DNP-modified B lymphoblastoid cells. Positive wells were expanded in IL2 and restimulated with autologous DNP-conjugated B lymphoblastoid cells every 14 days.

Lymphoproliferative Responses—PBL were tested as responder cells. They were suspended in lymphocyte culture medium (RPMI-1640, 10% pooled human AB$^+$ serum, insulin-transferrin-selenite media supplement (Sigma Chemical Co.) 2 mM L-glutamine, 1% non-essential amino acids, 25 mM HEPES buffer, penicillin+streptomycin) and added to 96-well, round bottom microliter plates at $1 \times 10^5$ cells/well. Stimulator cells included: 1) autologous or allogeneic PBL, 2) autologous or allogeneic B lymphoblastoid lines made by transfection with Epstein-Barr virus, 3) autologous cultured melanoma cells; they were inactivated by irradiation (5000 R). In most experiments, the responder:stimulator ratio was 1:1. The plates were incubated in a $CO_2$ incubator at 37° C. for 5 days; then the wells were pulsed with $^{121}$I-labeled IUDR (ICN Radiochemical, Costa Mesa, Calif.) for 6 hours, harvested with an automatic harvesting device, and counted in a gamma counter. The mean of triplicate wells was calculated. Cultured T cells were also tested for a lymphoproliferative response in accordance with the above methods.

Figure 3:
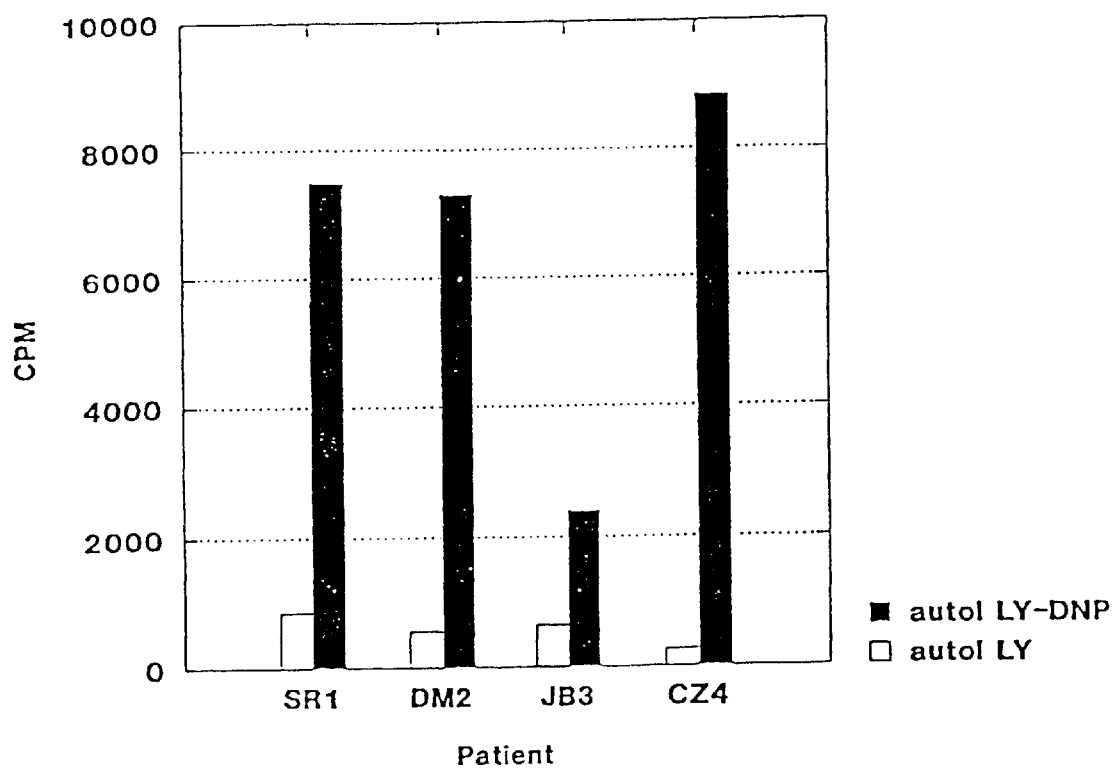
FIG. 3 is a graph of proliferative response of PBL to DNP-modified autologous lymphocytes. PBL were obtained from four patients receiving DNP-vaccine at the peak of their DTH responses. The cells were tested for ability to proliferate to DNP modified autologous PBL (autol LY-DNP) with unmodified autologous PBL (autol LY) as a control. Cultures were pulsed with $^{125}$IUDR on day 6.
Figure 4:
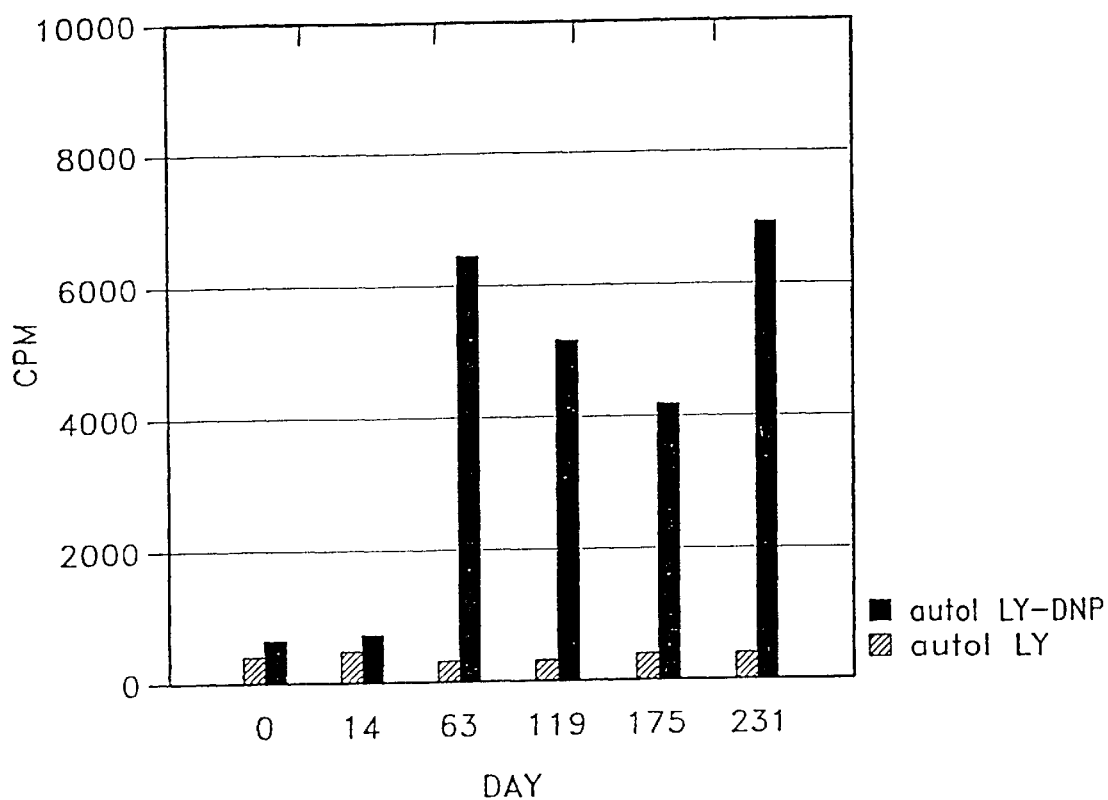
FIG. 4 shows the kinetics of the proliferative response to DNP-modified lymphocytes. PBL were serially collected from patient DM2 while receiving DNP vaccine. They were cryopreserved and then all samples were tested simultaneously for proliferative response to DNP-modified autologous PBL (autol LY-DNP). Cultures were pulsed with $^{125}$IUDR on day 6.

PBL, obtained and cryopreserved from four patients at the time of maximum DTH reactivity to DNP-modified autologous cells, were thawed and tested for in vitro proliferative responses. PBL from all four patients proliferated upon stimulation with DNP-modified cells (FIG. 3). The kinetics of the development of the proliferative response in one of these patients (DM2) is shown in FIG. 4. DNFB application alone (day 14) did not result in detectable numbers of circulating responding cells. Reactive PBL were detected after two injections of DNP-vaccine (day 63) and continued to be detected throughout the 8 months period of vaccine treatment.

Figure 5:
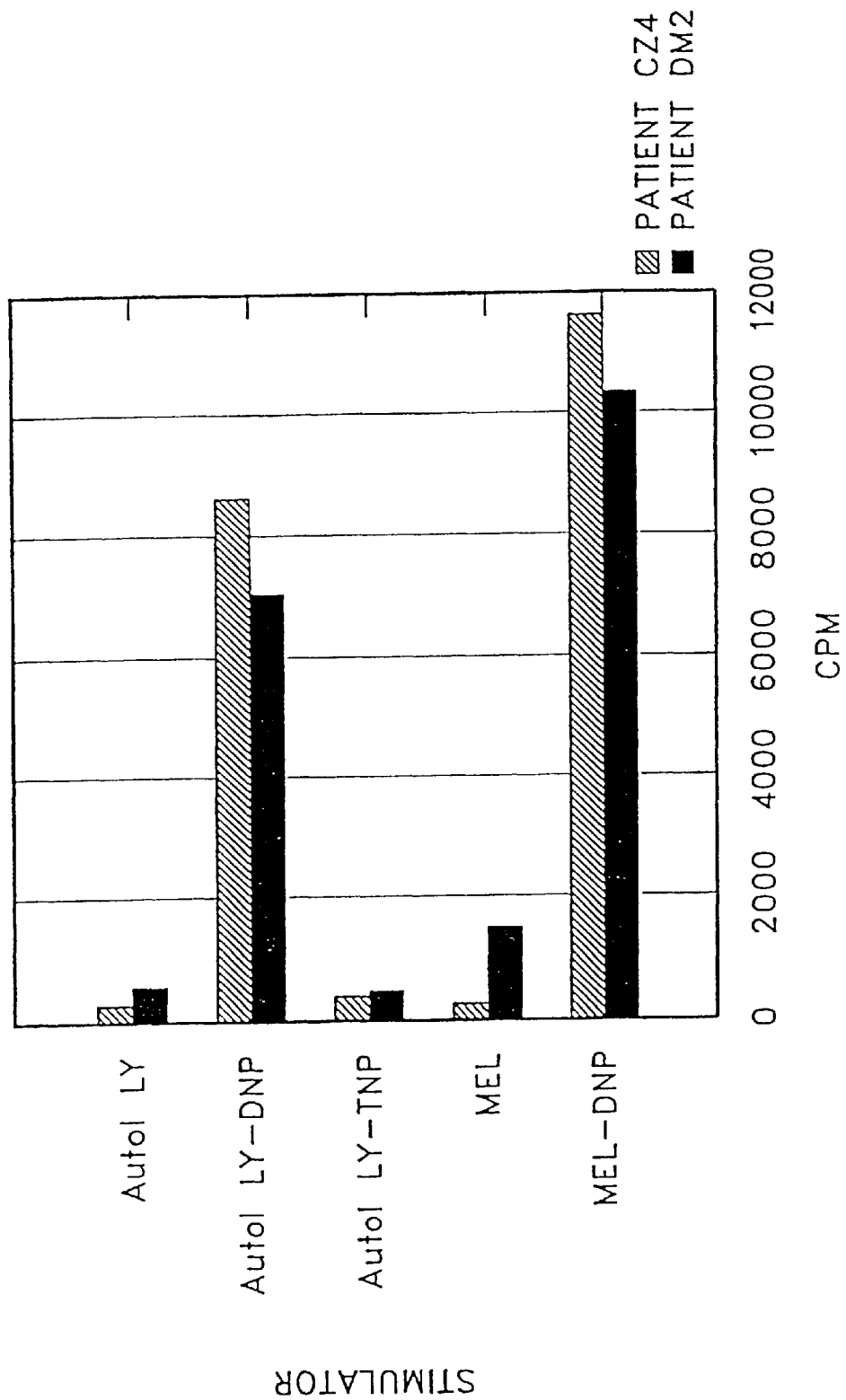
FIG. 5 displays specificity of the proliferative response to DNP-modified cells. PBL from two patients were tested for proliferative response to autologous PBL, either unmodified (autol LY), DNP-modified (autol LY-DNP), or TNP-modified (autol LY-TNP), and to cultured autologous melanoma cells, either unmodified (MEL) or DNP-modified (MEL-DNP). Cultures were pulsed with $^{125}$IUDR on day 6.

The proliferative response to DNP-modified cells was specific, since neither unconjugated PBL nor PBL modified with TNP evoked responses (FIG. 5). Post-vaccine PBL also proliferated briskly when stimulated with a DNP-modified melanoma cell line derived from autologous tumor tissue. When stimulated with allogeneic lymphocytes, PBL exhibited the expected mixed lymphocyte reaction which was three to five-fold greater than the DNP responses.

Figure 6:
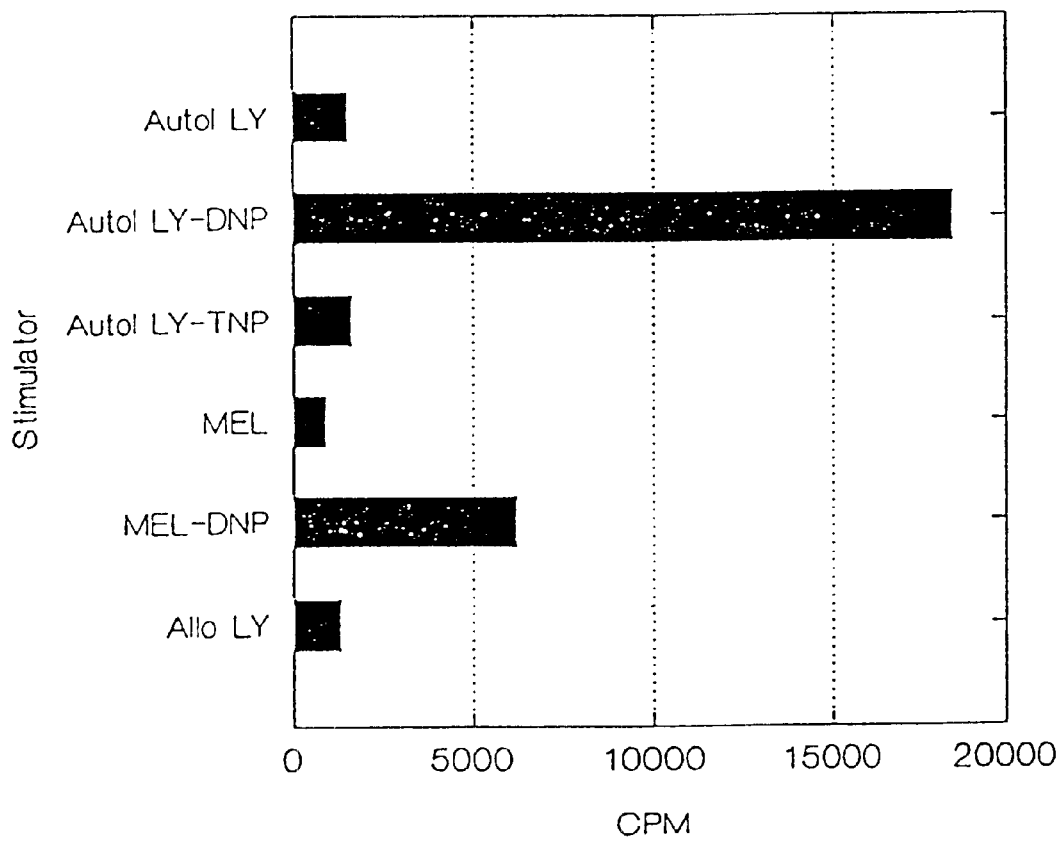
FIG. 6 is a specificity analysis of expanded T cells. PBL from patient DM2 were expanded in IL2 and repeatedly stimulated with autologous DNP-modified B lymphoblastoid cells. They were tested for proliferative response to autologous PBL, either unmodified (autol LY), DNP-modified (autol LY-DNP), or TNP-modified (autol LY-TNP); cultured autologous melanoma cells, either unmodified (MEL) or DNP-modified (MELDNP); and allogeneic PBL (Allo LY). Cultures were pulsed with $^{125}$IUDR on day 6.
Figure 7:
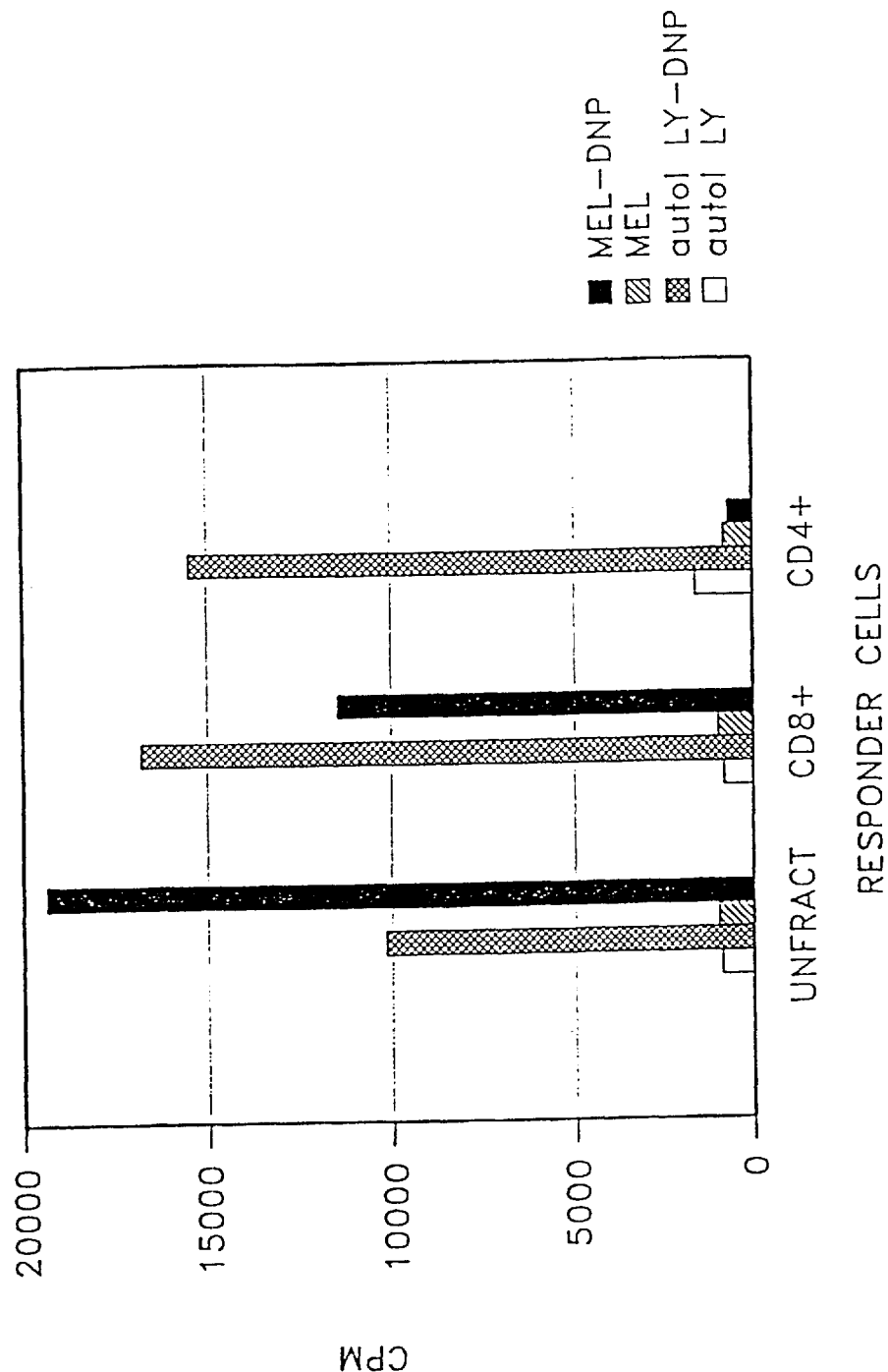
FIG. 7 displays responses of CD8+ and CD4+ T cells to DNP-modified autologous cells. Expanded T cells were separated into CD8-enriched or CD4-enriched populations by positive panning. Then they were tested for proliferative response to autologous PBL, either unmodified (autol LY), DNP-modified (autol LY-DNP), and to cultured autologous melanoma cells, either unmodified (MEL) or DNP-modified (MEL-DNP). Cultures were pulsed with $^{125}$IUDR on day 6.

Circulating T lymphocytes from one of these patients (DM2) were expanded in vitro by culture in IL2 and repeated restimulation with autologous DNP-modified B lymphoblastoid cells. After four weeks of expansion, the T cells were 70% CD3+, CD8+ and 30% CD3 +, CD4+. They proliferated when stimulated by autologous, DNP-modified B lymphoblastoid cells or DNP-modified, cultured melanoma cells, but not by unconjugated autologous cells (FIG. 6). These cells were separated by positive panning into CD8-enriched and CD4-enriched populations that were 98% pure as determined by flow cytometry analysis. As shown in FIG. 7, both CD4-enriched and CD8-enriched T cells exhibited a proliferative response to DNP-modified autologous B lymphoblastoid cells. However, only CD8 +T cells responded to DNP-modified autologous melanoma cells. This result may have been due to the low constitutive expression (<5%) of MHC class II by the melanoma cell line.

Figure 8:
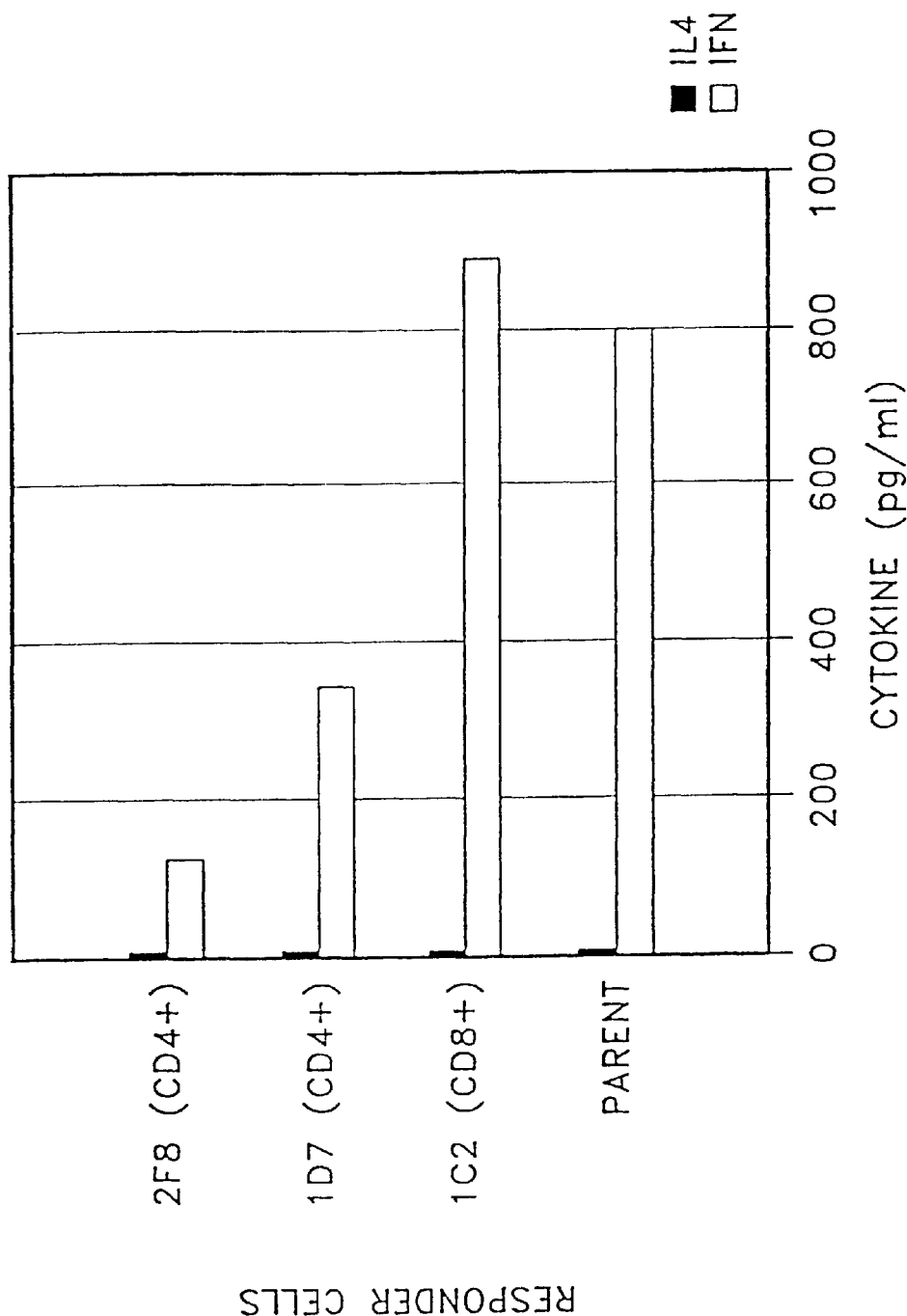
FIG. 8 shows cytokine production by DNP-reactive T cells. The DNP-reactive T cell line ("Parent"), and three subcultures (2F8, 1D7, 1C2), obtained by plating at limiting dilution, were incubated with autologous DNP-modified B lymphoblastoid cells for 18 hours; supernatants were collected and assayed for gamma interferon (IFN) and IL4.

Expanded T cells were tested for ability to produce cytokines when stimulated with autologous, DNP-modified B lymphoblastoid cells. As shown in FIG. 8, they produced gamma interferon but not IL4. To determine whether both CD4+ and CD8+ T cells were involved in the cytokine response, sublines that were obtained by plating T cells at limiting dilution were analyzed. Each of these cultures was homogeneous in respect to expression of CD4 and CD8. Three of these sublines (two CD4+, one CD8+) were tested for cytokine response to DNP-modified B lymphoblastoid cells. All three produced gamma interferon, while none made IL4 (FIG. 8).

Cytokine Production—T cells were added to round bottom microliter plates: at $1 \times 10^5$ cells/well. An equal number of stimulators (DNP-modified autologous B lymphoblastoid cells) was added, and supernatants were collected after 18 hours incubation. Commercially available ELISA kits were used to measure gamma interferon (Endogen, Boston, Mass.; sensitivity=5 pg/ml) and IL4 (R&D Systems, Minneapolis, Minn.; sensitivity=3 pg/ml).

To determine the MHC-dependence of the response, stimulator cells were pre-incubated with monoclonal antibodies to MHC class I (W6/32) or MHC class II (L243) at a concentration of 10 μg/ml for one hour before adding responder cells. Non-specific mouse immunoglobulin at the same concentration was tested as a negative control.

Figure 9:
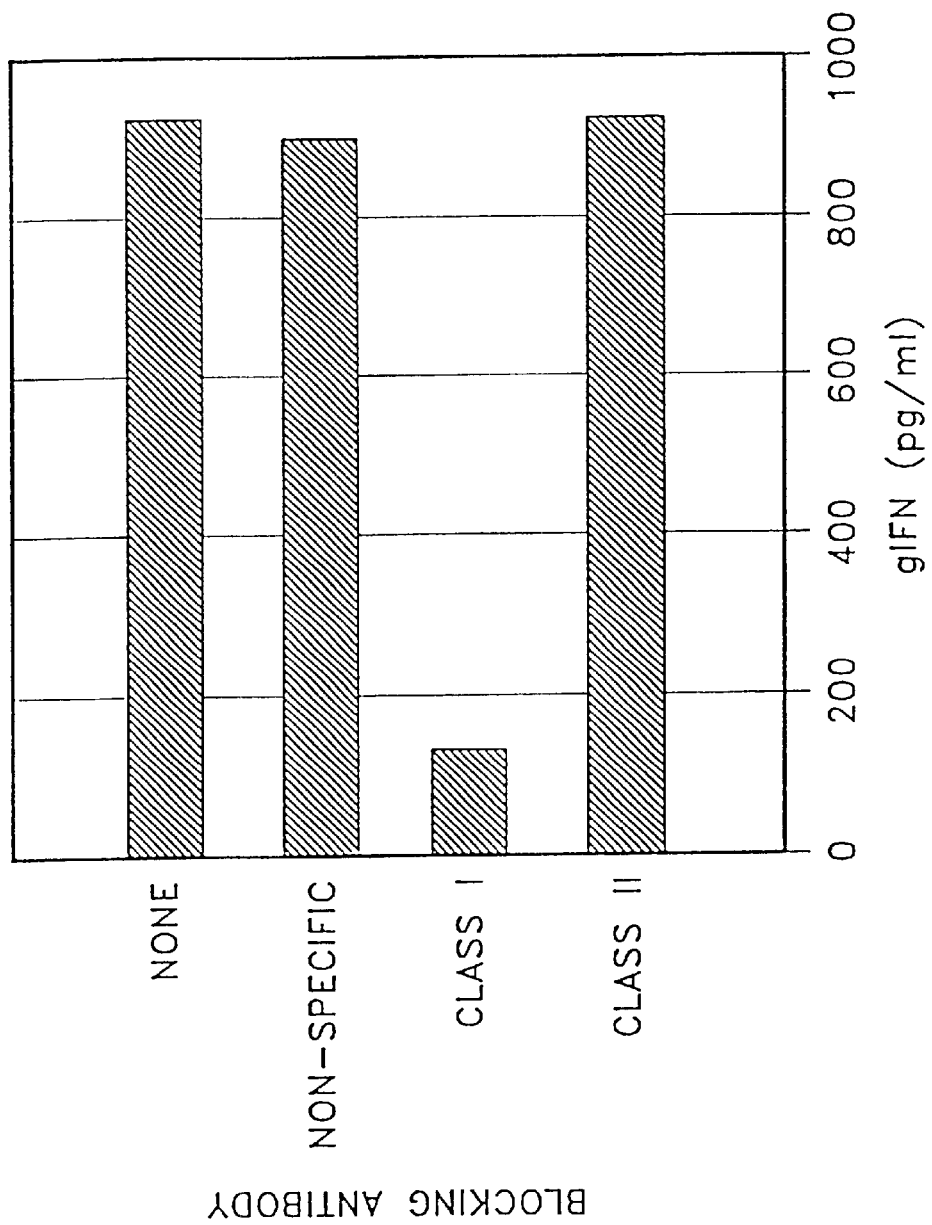
FIG. 9 shows blocking of T cell response by anti-MHC class I monoclonal antibody. Expanded CDB+ T cells were stimulated with autologous DNP-modified B lymphoblastoid cells and the cultures were assayed for gamma interferon after I 8 hours. Stimulator cells were preincubated with one of the following: no antibody (none), non-specific mouse IgG (non-specific), monoclonal antibody W6/32 (class I), or monoclonal antibody L243 (class II).
Figure 10:
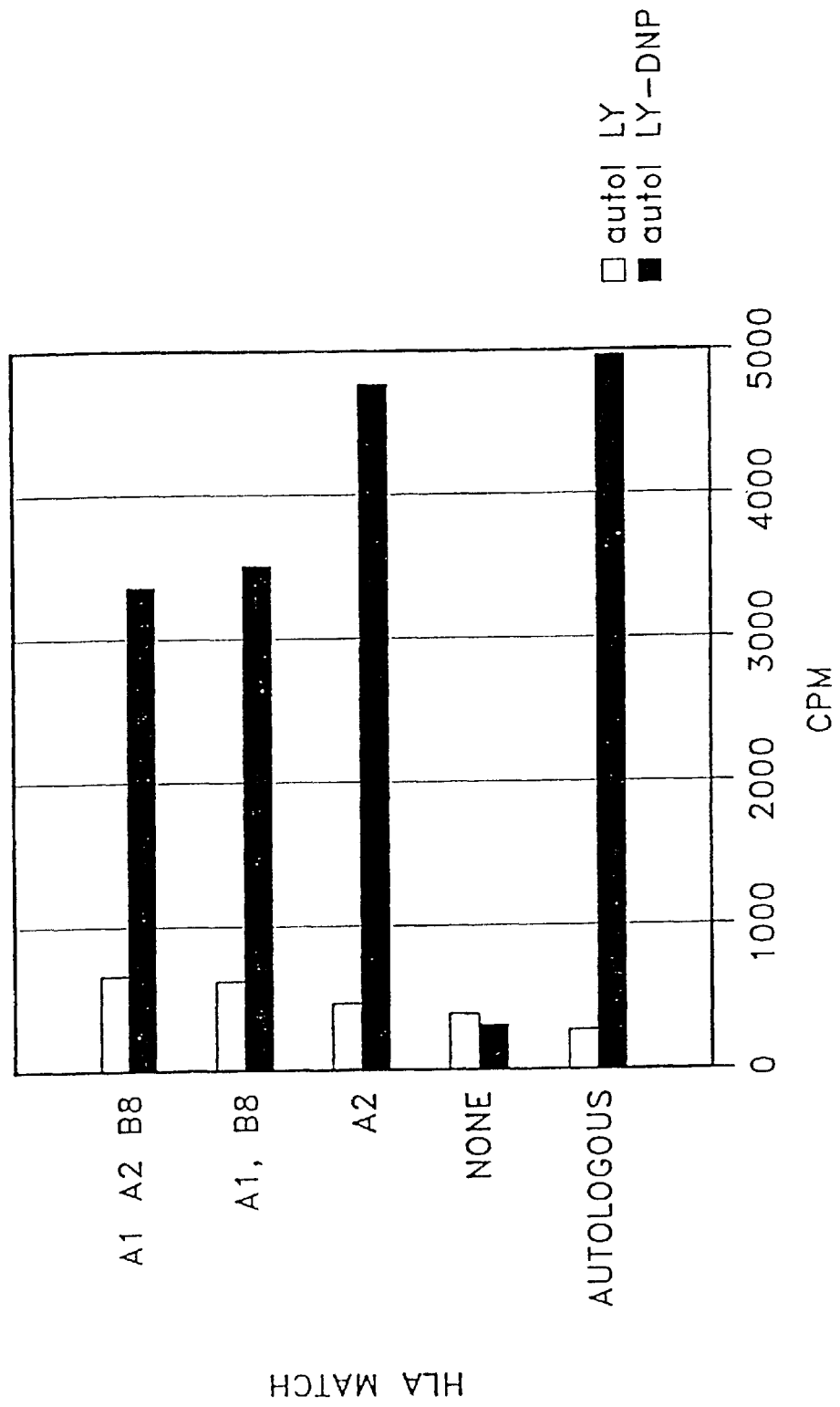
FIG. 10 exhibits MHC restriction of T cell response. Expanded CD8+ T cells (HLA-A1, A2, B8, Bw6) were tested for ability to proliferate in response to DNP-modified autologous PBL and to DNP modified allogeneic PBL from four other patients. Three of the allogeneic stimulators were matched at one or more class I loci as shown, and the fourth was completely mismatched (A24, A26, B44, B63). Cultures were pulsed with $^{125}$IUDR on day 6.

DNP-reactive CD8+ T cells obtained by panning of the bulk population were able to be maintained in long-term (>3 months) culture in IL2-containing medium by repeated stimulation,with DNP-modified autologous B lymphoblastoid cells; they retained the stable phenotype, CD3+, CD8+. Two lines of evidence confirmed that their response was MHC class I restricted: 1) Gamma interferon production was blocked by pre-incubation of stimulator cells with anticlass I framework antibody, but not by anti-class II antibody (FIG. 9), and 2). The T cells were able to respond to allogeneic DNP-modified stimulators that were matched at one or both HLA-A loci, but not to stimulators that were HLA-A mismatched. As shown in FIG. 10, T cells proliferated upon stimulation with DNP-modified autologous PBL (HLA-A1, A2, B8+, Bw6) and with DNP-modified allogeneic PBL that expressed A1 or A2 or both; no response was elicited by DNP-modified allogeneic stimulators that were A1 and A2 negative.

Figure 11A:
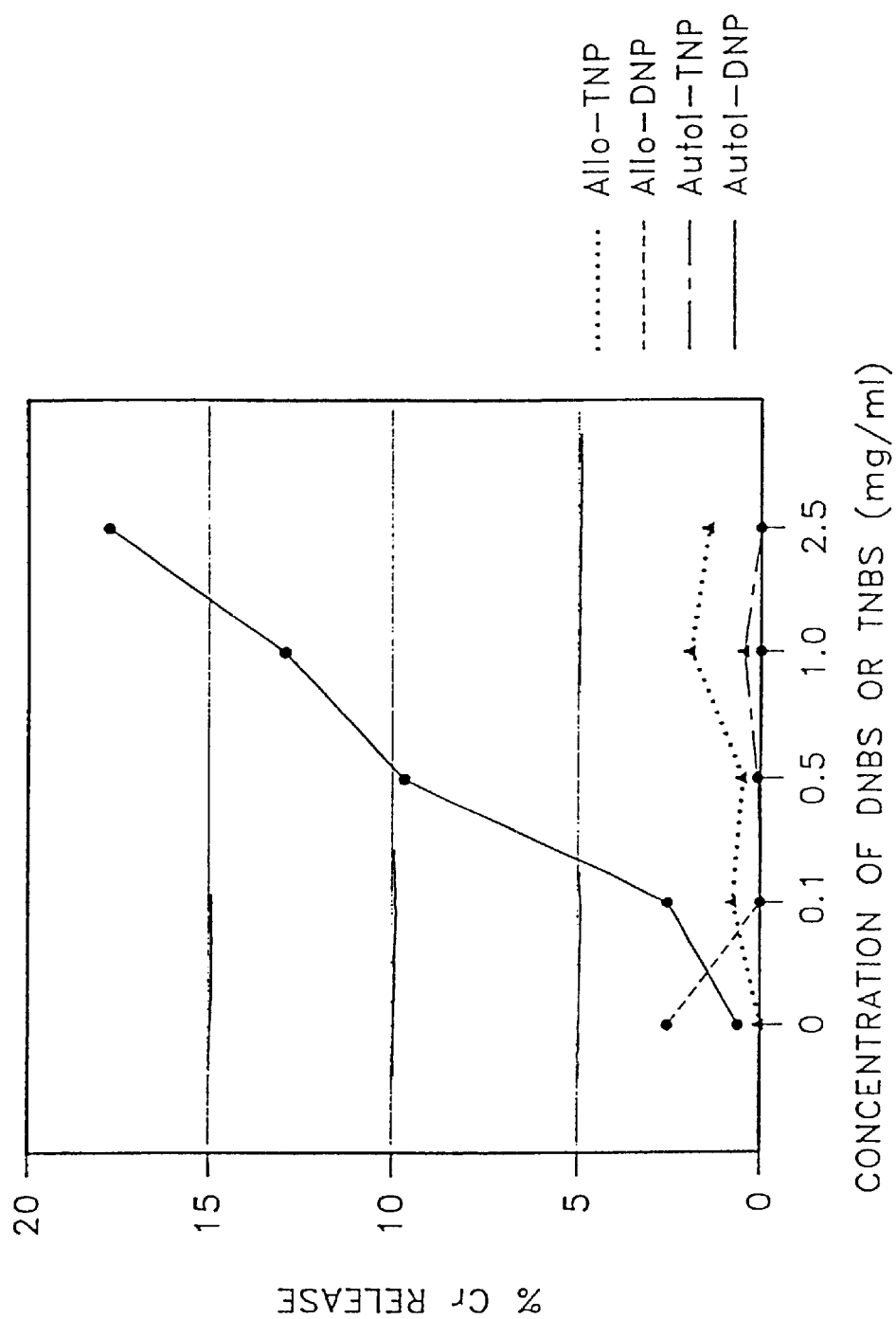
FIG. 11A—target cells were haptenized with various concentrations of DNBS or TNBS. The effector: target cell ratio was 20:1.
Figure 11B:
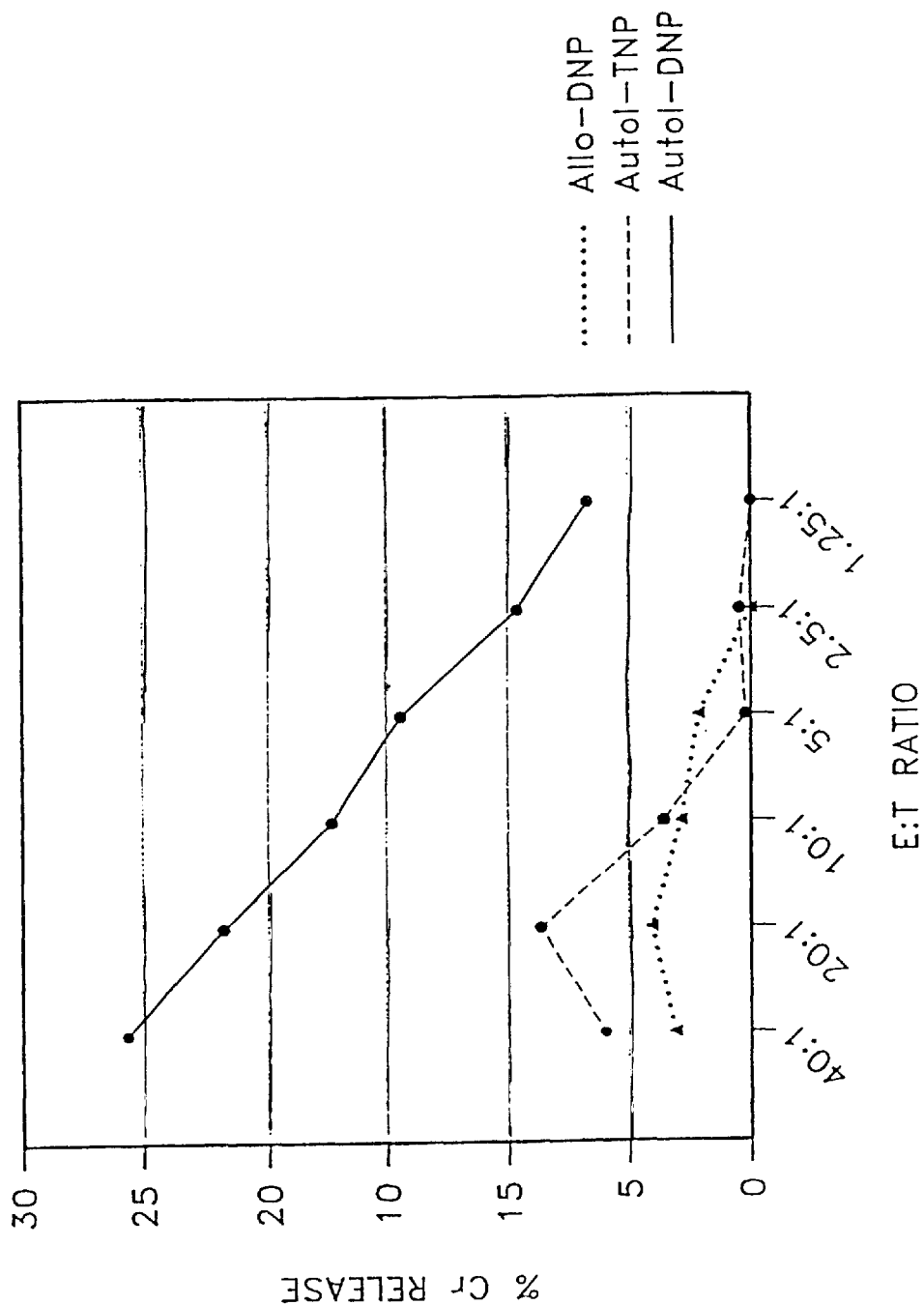
FIG. 11B—Target cells haptenized with 2.5 mg/ml DNBS or TNBS were mixed with effector cells at a series of effector: target (E:T) ratios.

Cytotoxicity—Melanoma targets were labeled for two hours with $^{51}$Cr (Amersham Corp, Arlington Heights, Ill.), and 2500 cells were added to round-bottom microliter wells. Then effector cells were added to achieve a series of E:T ratios. After 6 hours incubation at 37° C. supernatants were removed and counted in a gamma counter. Lysis was defined as: $[CPM_{test}-CPM_{spontaneous}]/[CPM_{total}-CPM_{spontaneous}])$ *100. The cytotoxicity of the CD8+T cell line was tested in a $^{51}$Cr-release assay with autologous melanoma cells as targets. To minimize spontaneous $^{51}$Cr release, DNP modification was accomplished with DNBS rather than DNFB. T cells lysed DNP-modified autologous melanoma cells but not allogeneic (class I-mismatched) melanoma cells (FIGS. 11a, 11b). There was a direct relationship between susceptibility to lysis and the degree of DNP modification, as determined by the concentration of DNBS used. Neither autologous nor allogeneic targets modified with TNP were lysed.

EXAMPLE 6

Clinical data was collected to suggest that an autologous, DNP-conjugated melanoma vaccine prolongs disease-free survival (DFS) and total survival (TS) in melanoma patients with bulky but resectable regional lymph node metastases. Forty-seven patients underwent standard lymphadenectomy with resection of metastatic masses. Tumor cells were enzymatically-dissociated from these tissues and cryopreserved. Vaccines consisted of $10 \times 10^6$ to $20 \times 10^6$ irradiated (2500 cGy) melanoma cells, conjugated to DNP and mixed with BCG. They were injected i.d. every 28 days for a total of 8 treatments. Cyclophosphamide 300 Mg/M$^2$ i.v. was given 3 days before the first 2 vaccines only. The DFS and TS of these patients were compared with those of 22 melanoma patients with resected nodal metastases treated previously with an unconjugated vaccine, see Example 4. Of 36 patients with stage 3 melanoma (palpable mass in one lymph node region), 22 are disease-free with a median follow-up of 33 months. Kaplan-Meir analysis projects a 3 year DFS and TS of 59% and 71%, respectively. In contrast, the DF8 and TS of stage 3 patients treated with unconjugated vaccine was 22% and 27% respectively (p=0.01, log-rank test). Of 11 stage 4 patients (palpable mass in two lymph node regions), 5 are NED (no evidence of disease) with a median follow-up of 41 months. For both stage 3 and 4 patients, the highest rate of relapse was in the first 6 months, a time when anti-melanoma immunity might not have yet been established. This experiment will be followed by an accelerated schedule of immunizations to reduce the rate of early relapses and improve the overall clinical outcome. The patients were compared to their condition prior to treatment with the vaccine. The patients treated prior to the vaccine study were removed from treatment one to two months prior to starting the vaccine study. Accordingly, the patients were untreated beginning the vaccine study.

EXAMPLE 7

Materials and Methods

Human melanoma tissue and cell lines—Tissue was obtained from patients with metastatic melanoma prior to entry into the vaccine program and at post vaccine time points. The clinical protocol for the DNP-vaccine administration was performed in accordance with Berd, D., et al., *Cancer Res.* 1991 51:2731–2734. Following surgery, the tumor specimen was transported to the laboratory, tumor tissue was isolated from surrounding fascia and connective tissue, and pieces of tumor measuring 2–4 mm$^3$ were snap frozen in liquid nitrogen. Melanoma cell lines from the same specimens were derived from enzyme digests (DNAase and collagenase) of the tumor and propagated as described by Berd, D., et al. *Cancer Res.* 1986 46:2572–2577.

Isolation of RNA and Amplification via RT-PCR—Total RNA was extracted from frozen tissues by grinding in guanidium isothiocyanate, followed by isolation using CsCl gradient as described by Lattime, E. C., et al., *J. Immunol.* 1988 144:3422–3428. To minimize the loss of tissue RNA, 15 μg of *E. coli* ribosomal RNA (Sigma Chemical Corp., St. Louis, Mo.) was added to each sample. Isolated RNA was resuspended in diethylpyrocarbonate treated (DEPC-tx) (Sigma) deionized distilled water. cDNA synthesis was performed using 10 μg total RNA, Random Primer (GibcoBRL, Gaithersburg, Md.), and RT buffer in DEPC-tx water. This was incubated at 65° C. for 10 min and then placed at 4° C. To this, 10 mM DTT (Gibco BRL), 0.5 mM each dATP, dCTP, dTTP, dTTP, (Gibco BRL), and 500 U MMLV-RT (Gibco BRL) was added to achieve a final reaction volume of 50 μl. Samples were incubated at 37° C. for 1 hour, then heated to 95° C. for 5 min.

For amplification by PCR, 5 μl of each cDNA was then added to MicroAmp reaction tubes (Perkin Elmer, Norwalk, Conn.) containing PCR Reaction buffer, 0.2 mM each dATP, dCTP, dGTP, dTTP, 1.25 U AmpliTaq DNA Polymerase (Perkin Elmer), MgCl$_2$ concentrations determined to be optimal for each primer pair (final concentrations of 1.5–6.0 mM), and 0.5 mM each of the appropriate primer pairs in a final volume of 50 μl. Primer pairs used in this study included beta-actin, TNF-alpha, IL-4, IFNγ, South San Francisco, Calif.) and IL10 (Clontech, Palo Alto, Calif.). P-actin served for a standard for comparison of relative mRNA expression between samples, as well as a control for RT and PCR reactions. PCR samples were amplified using a GeneAmp System 9600 thermocycler Perkin Elmer). Each sample was denatured at 94° C. for 37 sec, annealed at 55° C. for 45 sec, and extended at 72° C. for 60 sec for 39 cycles, followed by a 10 min. extension at 72° C.

PCR products and size markers (Novagen, Madison, Wis.) were separated in a 20% agarose gel (FMC BioProducts, Rockland, Me.). The gel was stained with ethidium bromide, visualized, and photographed under UV illumination. Electrophoresis of PCR products revealed a band corresponding to the predicted fragment size for each set of primers. Nonreverse transcribed RNA was subjected to amplification by PCR as a control for genomic DNA contamination.

Cryopreserved, enzyme-dissociated cell suspensions of melanoma tissues were found not to be suitable for RNA analysis. These samples usually expressed mRNA for all cytokines tested, probably a result of activation by the dissociation process.

Histology and In-Situ RT-PCR—Routine H&E staining of representative specimens was done by the Department of Pathology. In situ RT-PCR was done on paraffin sections which were permeablized using proteinase K, treated with reverse transcriptase and the resultant IL10 DNA amplified using the same primers as noted above using; methodology according to Bagasra, O., et al., *J. Immunol. Meth.* 1993 158:131–145.

Figure 14A:
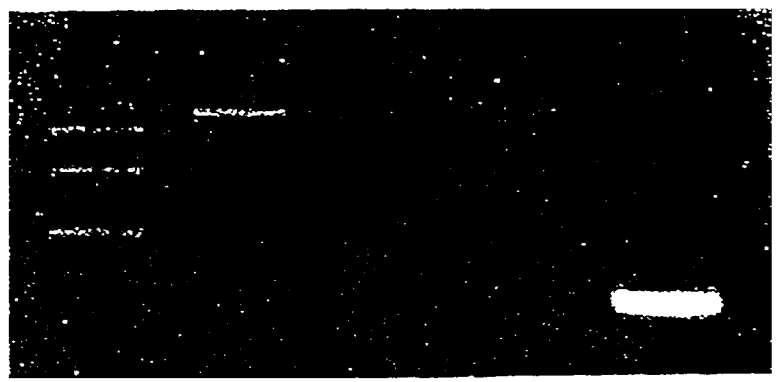
FIGS. 14A–14B displays an inflamed subcutaneous melanoma nodule from DNP-vaccine immunized patient expresses mRNA for IFNγ and IL10.
Figure 14B:
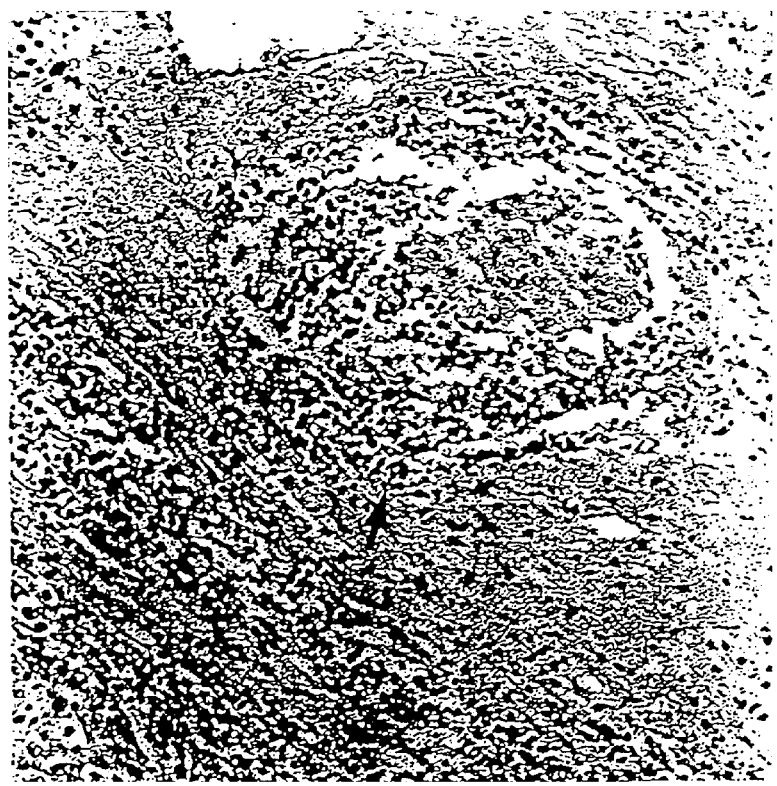

Cytokine mRNA in Inflamed. Post-vaccine biopsies—While metastatic melanoma is characterized by a paucity of lymphocytic infiltration (Elder et al., "The surgical pathology of cutaneous malignant melanoma." In: W. H. Clark, Jr., et al. (Eds.), *Human Malignant Melanoma,* pp. 100, New York: Grune and Stratton 1979), administration of DNPvaccine induces T cells infiltration in metastatic masses (Berd et al., 1991 supra.) Eight (8) subcutaneous metastases (from 4 patients) that had developed inflammation following vaccine treatment were studied and compared with 3 subcutaneous metastases excised before vaccine and 4 postvaccine metastases that failed to develop an inflammatory response. Post-vaccine, inflamed biopsies contained mRNA for IFNγ (5/8), IL4 (4/8) or both (3/8). In contrast, neither IFNγ mRNA nor IL4 mRNA was detected in the 7 control specimens. All but one of these 15 tissues expressed mRNA for IL10. FIG. 14 shows cytokine mRNA expression for a representative, T cell-infiltrated post-vaccine biopsy along with the corresponding histology.

Figure 15A:
FIGS. 15A–15B exhibits a lymph node metastasis from an unimmunized patient expresses mRNA for IL10 but not IFNγ.
Figure 15B:

Lymph Node Metastases—A group of biopsies of melanoma lymph node metastases was studied as well. Histologically, these lesions are characterized by an abundance of lymphocytes (FIG. 15B) that are thought to be the residua of the tumor-infiltrated lymph node lymphocytes (Cardi, et al., *Cancer Res.* 1989 49:6562–6565). Of the 10 lymph node biopsies studied, only one expressed mRNA for INFγ; this specimen, and one additional specimen, contained mRNA for IL4. However, all 10 specimens contained mRNA for IL10. FIG. 15 shows cytokine mRNA expression for a representative lymph node metastasis along with the corresponding histology.

Figure 16:
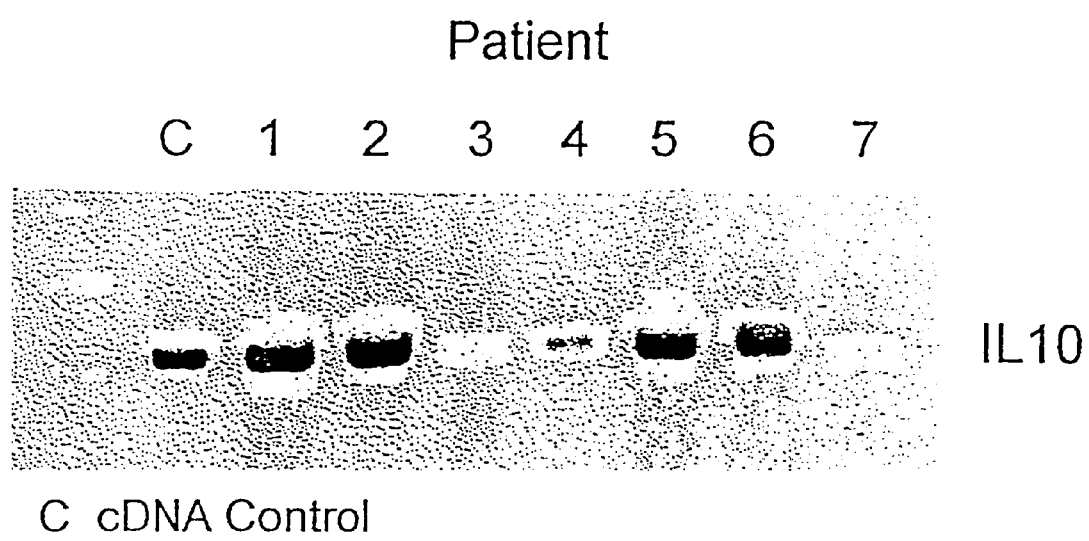
FIG. 16 is a gel of IL10 mRNA expressed in human melanoma metastases. mRNA for cytokines was determined by RT-PCR (lane 1=size marker; C=IL10 cDNA control; 1–7=patient samples).
Figure 17:
FIG. 17 is a gel of IL10 mRNA expressed by the melanoma cells.
Figure 18A:
FIGS. 18A–18B is an in-situ RT-PCR from a paraffin section of a non-inflamed melanoma biopsy (A=100×, B=400×).
Figure 18B:
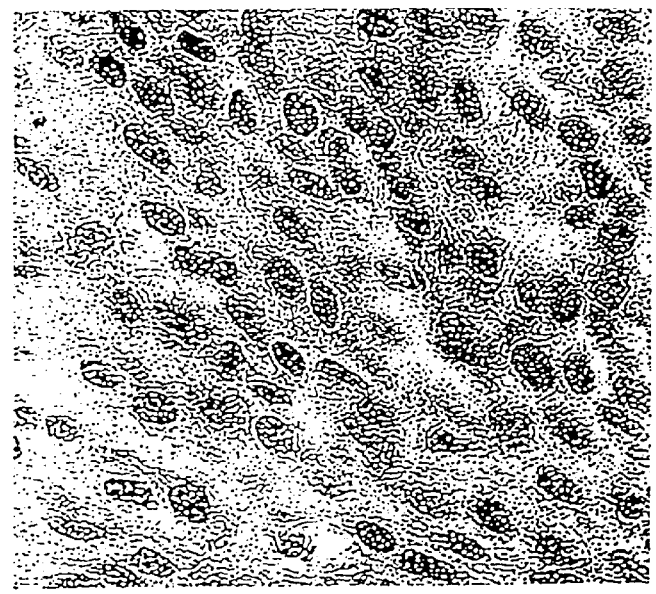

IL10 Production by Melanoma Metastasis and Cell Lines—As indicated above, IL10 mRNA expression was seen in 24/25 melanoma metastases (FIG. 16). Since it was independent of INFγ or IL4 mRNA expression and did not correlate with T cell infiltration, melanoma cells, rather than lymphocytes, may be the source of:IL10. Two approaches were used to test this hypothesis. First, cell lines derived from two of the metastatic tumors described above were examined. As illustrated in FIG. 17A, both the cell lines and the tissue from which they were derived expressed IL10 mRNA.

Both cell lines produced IL10, as determined by assay of culture supernatants after a 72 hour incubation (IL10 concentrations: 760 pg/ml and 10 pg/ml, respectively). Second, IL10 mRNA expression on a tissue section of a melanoma metastasis was studied using in situ RT-PCR. As seen in FIG. 17B, IL10 mRNA is associated in melanoma cells and not in non-tumor elements.

TNF mRNA is expressed in melanoma metastasis— mRNA for TNF in human colon carcinoma biopsies using in situ hybridization (Naylor, M. S., et al., *Cancer Res.* 1990 50:4436–4440), and that resistance to TNF is associated with in vivo tumor growth (Lattime, E. C. and Stutman, O., *J. Immunol.* 1989 143:4317–4323). TNF mRNA was detected in 6/23 melanoma specimens. There was an association with DNPvaccine-induced inflammation: 4/7 T cell-infiltrated post-vaccine biopsies were positive versus 2/16 pre-vaccine or non-infiltrated post-vaccine specimens.

EXAMPLE 8

This example discloses dinitrophenyl modified tumor peptides for cancer immunotherapy.

Epstein barr virus (EBV) was added to B lymphoblastoid cells in culture. The B lymphoblastoid cells were transformed into a B cell tumor from the patient's own a lymphocytes. Melanoma from a metastasis was cultured in RPMI 1640+10% fetal calf serum or 10% pooled human serum. The non-adhered cells were washed off with RPMI medium. When the cells were confluent, they were detached with 0.1% EDTA and passaged into two flasks. This process continued for about 10 to about 30 passages. To test for gamma interferon production by T cells, lymphocytes from a patient's blood were obtained. About 1,000,000 lymphocytes were mixed with DNP modified autologous melanoma cells to stimulate T cells. Every seven days, 100 U/ml of interleukin-2 was added. The T cells were expanded by passage as disclosed above. The T cells were then restimulated by the DNP modified autologous melanoma cells. An enriched population of T cells resulted which were responsive to the DNP modified autologous melanoma cells. Stimulation was determined by the amount of gamma interferon production by the T cells. Generally the production of gamma interferon at greater than 15 picograms/ml was considered. These T cells were then used to test the peptide.

Small peptides were extracted from 4 types of cells, all generated from a single patient: 1) B lymphoblastoid cells, 2) B lymphoblastoid cells modified with dinitrophenyl (DNP), 3) cultured melanoma cells, 4) cultured melanoma cells modified with DNP. Cells were suspended in 0.1% trifluoroacetic acid, dounced, sonicated, and centrifuged at 100,000×g for 90 minutes. Material in the supernatant of molecular weight>10,000 was removed by a Centricon 10 filter. The remaining material was separated on a reversed phase HPLC column. Individual fractions were collected, dried, resuspended in culture medium, and added to autologous B lymphoblastoid cells, which bound and presented the peptides. These peptide-pulsed B cells were tested for ability to stimulate a T lymphocyte cell line that was specifically sensitized to autologous DNP-modified melanoma cells.

Figure 13:
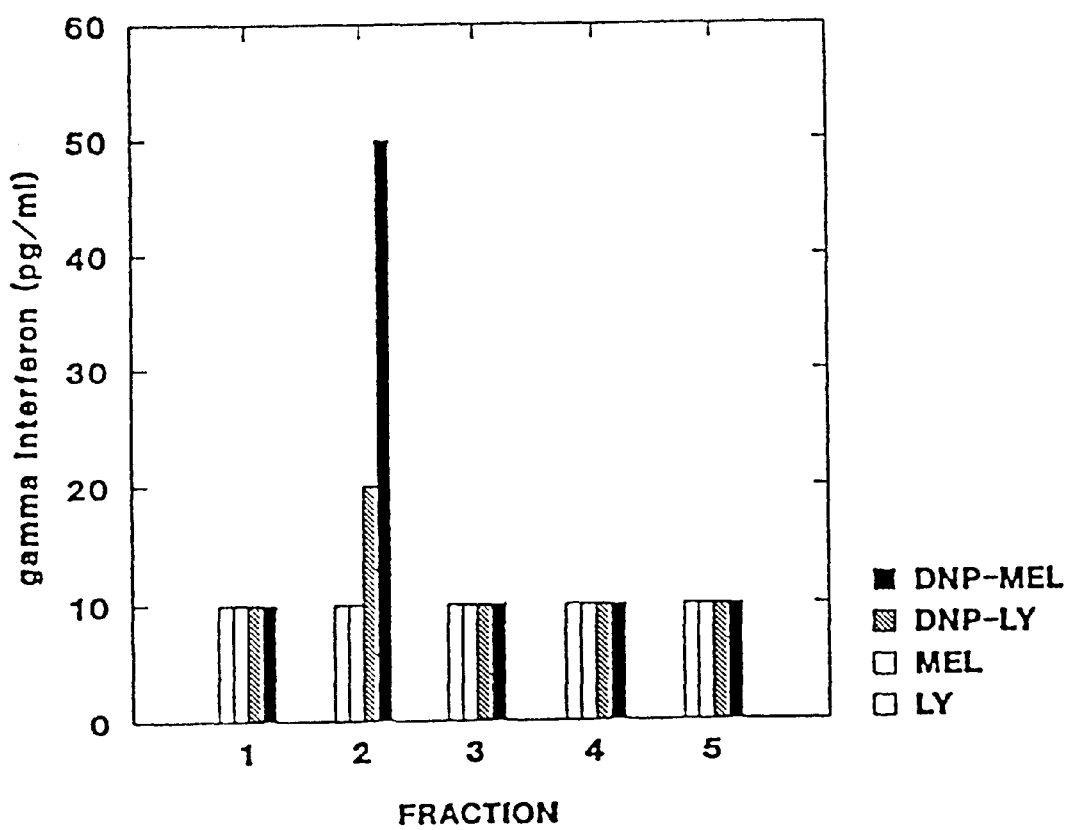
FIG. 13 shows the HPLC fractions which were pooled into five groups of ten fractions each. Peptides derived from dinitrophenyl modified melanoma cells (DNP-MEL) or dinitrophenyl modified B cells (DNP-LY) were stimulatory in pool 2.

Initially the 50 HPLC fractions (10µl of each sample) were pooled; into five groups of ten fractions each. As shown in FIG. 13, only peptides derived from DNP-modified melanoma cells (DNP-MEL) or DNP-modified B cells (DNP-LY) were stimulatory, and only pool #2 was positive.

Each of the individual fractions of pool #2 were analyzed by performing the T cell stimulation test with each fraction in pool 2; activity was found only in fractions #17 and #18, and DNP-MEL peptide stimulated two-fold more gamma interferon production than DNP-LY.

These results indicate that a single HPLC fraction of low molecular: weight peptide preparation contains the peptide or peptides responsible for stimulation of T cells sensitized to DNP modified melanoma cells.

EXAMPLE 9

This example will determine peptide stimulation inhibition by anti-DNP antibody.

The experiment will be identical to that described for Example 8 with one exception. After adding peptide to the B lymphoblastoid cells, and just before adding the responding T cells, varying concentrations (1–100µl/ml) of anti-DNP antibody will be added to different samples. The anti-DNP antibody may be obtained from the ATCC, hybridoma #CRL-1968, or a similar antibody. If the stimulation is caused by DNP modified peptides, the antibody will inhibit it. It is expected that fractions 17 and 18 will be inhibited by the antibody.

EXAMPLE 10

Example 10 is expected to determine whether the responding T cells are CD4+or CD8+.

The experiment will be identical to that described for Example 8 with one exception. The responding T cells will be fractionated into subsets before being added to the peptide-pulsed B lymphoblastoid cells. This is accomplished by mixing the T cells with magnetic beads coated with either anti-CD4 or anti-CD8 antibodies (obtained commercially from Immunotech, Inc., Westbrook, Me.). Then the beads, and the cells that have bound to them are removed with a magnet. The non-binding cells are washed in tissue culture medium (RPMI+10% pooled human serum) , counted, and added to the microliter wells for measurement of stimulation.

EXAMPLE 11

Example 11 discloses dinitrophenyl-modified tumor membranes for cancer immunotherapy.

Membranes from cultured melanoma cells from one patient have been prepared according to the method of Heike et al., *J. Immunotherapy* 1994 15:165–174, the disclosure of which is incorporated herein by reference in its entirety. The melanoma cells were conjugated to dinitrophenyl (DNP) according to the methods of Miller and lies Claman, *J. Immunology* 1976 117:1519–1526, the disclosure of which is incorporated by reference, in its entirety. The cells were suspended in 5 volumes of 30 mM sodium bicarbonate buffer with 1 mM phenyl methyl sulfonyl fluoride and disrupted with a glass homogenizer. Residual intact cells and nuclei were removed by centrifugation at 1000 g. Then the membranes were pelleted by centrifugation at 100,000 g for 90 minutes. The membranes were resuspended in 8% sucrose and frozen at −80° C. until needed. Melanoma cells were similarly prepared for conjugation to dinitrophenyl.

These DNP modified melanoma cell membranes were tested for their ability to stimulate autologous T lymphocytes that had been sensitized to DNP modified intact melanoma cells. This was done by incubating about 100,000 T lymphocytes/well with about 10,000–about 100,000 cell equivalents DNP modified membranes/well, and measuring production of gamma interferon production (greater than 15 picograms). This process was repeated by incubating the T lymphocytes with DNP modified melanoma cells. The results revealed that intact melanoma cells and the membranes derived from them were equally effective in stimulating T cells.

This experiment, which has been repeated several times (using the same patient sample) with similar results, indicates that DNP modified melanoma membranes can substitute for DNP modified intact melanoma cells in inducing a T cell response.

EXAMPLE 12

Example 12 will determine if addition of autologous monocytes or dendritic cells augments the T cell response to tumor membranes.

Autologous monocytes will be isolated as follows. Peripheral blood lymphocytes will be separated from peripheral blood by gradient centrifugation according to the methods of Boyum, A., Scand. *J. Clin. Lab. Invest.* 21, 1968 Suppl 97:77–89, the disclosure of which is incorporated herein by reference in its entirety. They will be suspended in tissue culture medium (RPMI-1640+10% pooled human serum) and added to plastic microliter wells for about two hours in order for monocytes to adhere. Then the nonadherent cells will be washed off with culture medium. Various concentrations of GM-CSF (granulocyte macrophage colony stimulating factor, obtained commercially from Immunex, Seattle, Wash.) will be added to stimulate growth of the monocytes. After about 2–3 weeks, the monocytes, now considered macrophages, will be removed from the plastic with 0.1% EDTA and added in graded numbers (about 100 to about 10,000/well) to fresh microtiter wells. Graded numbers of membranes, prepared from DNP modified autologous tumor cells (quantified as cell equivalents), will be added to the adherent macrophage monolayer. After about 6 to about 24 hours, DNP specific autologous T cells will be added and incubated for an additional 24 hours. Then supernatants will be collected and tested for production of cytokines such as and not limited to gamma interferon, IL2, tumor necrosis factor; or for proliferation or stimulation of T cells such as by thymidine, or with dyes such as MTT. For example, $^{125}$IUDR will be added and the cells will be collected on an automatic harvesting device to test for T cell proliferation. Controls will consist of unstimulated T cells and T cells stimulated with membranes in the absence of macrophages. The ability of autologous dendritic cells to enhance the response to membranes will be tested in the same manner. Dendritic cells will be isolated from peripheral blood mononuclear cells and grown in tissue culture according to the method of O'Doherty, U., et al., *J. Exp. Med.* 1993 178:10678–1078, the disclosure of which is incorporated herein by reference in its entirety.

EXAMPLE 13

Example 13 is expected to determine whether patients who received DNP modified melanoma vaccine manifest delayed type hypersensitivity (DTH) to autologous DNP-modified melanoma membranes.

The study subjects will be patients who have received repeated doses of DNP modified melanoma cell vaccine. Membranes will be prepared from autologous DNP modified melanoma cells as described above. Graded numbers of membranes (about 100 to about 10,000 cell equivalents) will be washed in PBS, resuspended in PBS, and injected intradermally on the forearm. DTH will be measured about 48 hours later as the diameter of cutaneous induration. Controls will consist of autologous unconjugated melanoma cell membranes and membranes prepared from autologous blood lymphocytes.

EXAMPLE 14

Example 14 is expected to determine whether macrophages or dendritic cells process allogeneic melanoma membranes and present them in an immunogenic manner to T cells syngeneic to those macrophages.

The procedure will be similar to that described for Example 12 with the exception that the stimulating membranes will be prepared from allogeneic DNP conjugated melanoma cells. The hypothesis is that macrophages or dendritic cells from patient A can in vitro process membranes obtained from the melanoma cells of patient B. This results in stimulation of T cells from patient A. This experiment may lead to a strategy for allogeneic immunization. DNP modified membranes prepared from a single allogeneic melanoma cell line, or pool of allogeneic cell lines, would be processed by a patient's macrophages or dendritic cells in vitro. Those cells would be used for immunization.

EXAMPLE 15

Administration of a vaccine consisting of autologous melanoma cells. modified with the hapten, dinitrophenyl (DNP-vaccine), prolonged relapse-free and overall survival in patients with clinical stage three melanoma following lymphadenectomy. The following four dosage-schedules of DNP-vaccine in post-surgical adjuvant patients were compared to determine their efficacy in inducing DTH to autologous, unmodified melanoma cells (autol-MEL): (1) Schedule A, according to which a total of eight vaccines was administered each every 28 days (all vaccines were DNP-modified); (2) Schedule B, according to which a total of 12 vaccines was administered weekly and alternating DNP-modified and unmodified vaccine; (3) Schedule C, according to which a total of 12 vaccines was administered weekly, (all vaccines were DNP-modified); and Schedule D, according to which a total of six vaccines was administered weekly (all vaccines were DNP-modified). Patients on all schedules except D were sensitized to the hapten prior to vaccine. In all four regimens BCG was mixed with the melanoma cells to provide an immunological adjuvant. Patients on schedule C received three doses of cyclophosphamide at spaced apart intervals during the treatment. Patients on schedule D received only one dose of cyclophosphamide before the first vaccine.

Surprisingly, dosage-schedules A and D induced significantly greater DTH to autol-MEL than the more intensive schedules, B and C (p=0.001, Mann-Whiten U tests). The percentage of patients who developed a DTH response to autol-MEL$\geq$m5 mm was as follows: Schedule A: 45% (20 patients of total 44, i.e., 20/44), Schedule B: 11% (3/27), Schedule C: 18% (4/22), Schedule D: 59% (16/27) (p<0.01, Chi square). In contrast, all four dosage-schedules induced similar DTH responses to PPD. Follow-up to date suggests that the two dosage-schedules (A and D) that were most effective in inducing DTH to autol-MEL produced longer relapse-free survivals than the two schedules (B and C) that were less immunologically effective, even after adjusting for standard prognostic variables. Thus, the dosage and schedule of administration of human tumor vaccines may be important inducing immunological responses that have clinical meaning.

The disclosures of each patent, patent application and publication cited or described in this document are hereby incorporated herein by reference, in their entirety.

Various modifications of the invention in addition to those shown and described herein will be apparent to those skilled in the art from the foregoing description. Such modifications are also intended to fall within the scope of the appended claims.

What is claimed is:

1. A method for inducing an anti-tumor response in a mammalian patient suffering from a tumor, which method comprises administering to said patient a composition comprising a tumor cell or tumor cell extract with an adjuvant, wherein the tumor cell or tumor cell extract is;
    (i) conjugated to a hapten;
    (ii) of the same tumor type as the patient's tumor;
    (iii) not allogeneic to said patient; and
    (iv) incapable of growing in the body of the patient after injection;
    and repeating said administration at weekly intervals, wherein a therapeutically effective amount of cyclophosphamide is administered only prior to the first administration of the composition, wherein the patient is not sensitized to the hapten prior to administration of the composition, and wherein the composition elicits an anti tumor response.

2. The method of claim 1, wherein said composition is administered for at least three times.

3. The method of claim 1, wherein said composition is administered for at least six times.

4. The method of claim 1 wherein said therapeutically effective amount of cyclophosphamide comprises administering a dose of about 300 mg/M$^2$ of cyclophosphamide.

5. The method of claim 1 wherein said tumor cell or extract is selected from the group consisting of melanoma, lung, colon, breast, kidney, prostate, ovarian and leukemia tumor cell or extract.

6. The method of claim 5, wherein said tumor cell or extract is a melanoma tumor cell or extract.

7. The method of claim 1 wherein said hapten is selected from the group consisting of dinitrophenyl, trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, trinitrobenzenesulfonic acid, sulfanilic acid, arsanilic acid, dinitrobenzene-S-mustard and combinations thereof.

8. The method of claim 7 wherein said hapten is dinitrophenyl.

9. The method of claim 1 wherein said adjuvant is selected from the group consisting of Bacillus Calmette-Guerin, QS-21, detoxified endotoxin and a cytokine.

10. The method of claim 1 wherein said mammalian patient is a human.

11. The method of claim 1 wherein said composition comprises at least $10^6$ tumor cells or cell equivalents extract per dose.

12. The method of claim 1 wherein said anti-tumor response is at least one of the following: tumor necrosis, tumor regression, tumor inflammation, tumor infiltration by activated T lymphocytes, stable disease and prolongation of patient survival.

13. The method of claim 1, wherein the cyclophosphamide is administered 3 days prior to administration of the composition.

14. The method of claim 1, wherein the composition comprises a maximum of $7.5 \times 10^6$ cells or cell equivalents per dose.

* * * * *

```
                              SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
atggatgatg atatcgccgc g                                                   21

<210> SEQ ID NO 2
<211> LENGTH: 33
<212> TYPE: DNA
<213> ORGANISM: Artificial Sequence
<220> FEATURE:
<223> OTHER INFORMATION: PCR primer

<400> SEQUENCE: 2
ctagaagcat tgcggtgga cgatggaggg gcc                                       33

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
atgaaatata caagttatat c                                                   21

<210> SEQ ID NO 4
<211> LENGTH: 33
<212> TYPE: DNA
<213> ORGANISM: Artificial Sequence
<220> FEATURE:
<223> OTHER INFORMATION: PCR primer

<400> SEQUENCE: 4
ttactgggat gctcttcgac ctcgaaacag cat                                      33

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
atgggtctca cctcccaact g                                                   21

<210> SEQ ID NO 6
<211> LENGTH: 33
<212> TYPE: DNA
<213> ORGANISM: Artificial Sequence
<220> FEATURE:
```

```
<223> OTHER INFORMATION: PCR primer

<400> SEQUENCE: 6
tcagctcgaa cactttgaat atttctctct cat                              33

<210> SEQ ID NO 7
<211> LENGTH: 32
<212> TYPE: DNA
<213> ORGANISM: Artificial Sequence
<220> FEATURE:
<223> OTHER INFORMATION: PCR primer

<400> SEQUENCE: 7
aagctgagaa ccaagaccca gacatcaagg cg                               32

<210> SEQ ID NO 8
<211> LENGTH: 31
<212> TYPE: DNA
<213> ORGANISM: PCRArtificial Sequence
<220> FEATURE:
<223> OTHER INFORMATION: PCR primer

<400> SEQUENCE: 8
agctatccca gagccccaga tccgattttg g                                31

<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9
atgagcactg aaagcatgat c                                           21

<210> SEQ ID NO 10
<211> LENGTH: 23
<212> TYPE: DNA
<213> ORGANISM: Artificial Sequence
<220> FEATURE:
<223> OTHER INFORMATION: PCR primer

<400> SEQUENCE: 10
tcacagggca atgatcccaa agt                                         23
```